United States Patent
Gemma et al.

(10) Patent No.: US 10,815,285 B2
(45) Date of Patent: Oct. 27, 2020

(54) RECOMBINANT ADENO-ASSOCIATED VIRUS-MEDIATED EXPRESSION OF FRACTALKINE FOR TREATMENT OF NEUROINFLAMMATORY AND NEURODEGENERATIVE DISEASES

(75) Inventors: Carmelina Gemma, Bellevue, WA (US); Paula C. Bickford, Ruskin, FL (US); Kevin R. Nash, Seffner, FL (US); Josh Morganti, Richmond, CA (US); Adam Bachstetter, Lexington, KY (US)

(73) Assignees: UNIVERSITY OF SOUTH FLORIDA, Tampa, FL (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 479 days.

(21) Appl. No.: 14/126,708

(22) PCT Filed: Jun. 30, 2012

(86) PCT No.: PCT/US2012/045158
§ 371 (c)(1),
(2), (4) Date: Mar. 14, 2014

(87) PCT Pub. No.: WO2013/006514
PCT Pub. Date: Jan. 10, 2013

(65) Prior Publication Data
US 2014/0205570 A1 Jul. 24, 2014

Related U.S. Application Data

(60) Provisional application No. 61/503,958, filed on Jul. 1, 2011.

(51) Int. Cl.
| | | |
|---|---|---|
| C07K 14/52 | (2006.01) |
| C07K 14/715 | (2006.01) |
| A61K 38/00 | (2006.01) |
| A61K 48/00 | (2006.01) |

(52) U.S. Cl.
CPC ........ C07K 14/521 (2013.01); C07K 14/7158 (2013.01); *A61K 38/00* (2013.01); *A61K 48/00* (2013.01); *C12N 2750/14143* (2013.01); *C12N 2750/14171* (2013.01)

(58) Field of Classification Search
CPC .. C07K 14/521; C07K 14/7158; A61K 38/00; A61K 48/00; C12N 2750/14143; C12N 2750/14171
See application file for complete search history.

(56) References Cited

U.S. PATENT DOCUMENTS

| | | | | |
|---|---|---|---|---|
| 6,503,888 B1 * | 1/2003 | Kaplitt | ................... | C07K 14/48 435/320.1 |
| 6,548,654 B1 * | 4/2003 | Hardiman | ............. | C07K 14/521 435/252.3 |
| 2005/0260164 A1 | 11/2005 | Jolly et al. | | |
| 2009/0092578 A1 | 4/2009 | Su et al. | | |
| 2009/0226435 A1 * | 9/2009 | Khare | ............... | A61K 47/48423 424/133.1 |
| 2012/0213809 A1 * | 8/2012 | Rome | .................... | A61K 38/00 424/185.1 |
| 2013/0195801 A1 * | 8/2013 | Gao | ........................ | C12N 15/86 424/93.2 |

OTHER PUBLICATIONS

Davidson et al. "Viral vectors for gene delivery to the nervous system." Nat Rev Neurosci. May 2003;4(5):353-64.*
Zhang et al. "Several rAAV vectors efficiently cross the blood-brain barrier and transduce neurons and astrocytes in the neonatal mouse central nervous system." Mol Ther. Aug. 2011;19(8):1440-8. doi: 10.1038/mt.2011.98. Epub May 24, 2011.*
Lowenstein, P. "Crossing the Rubicon." Nat Biotechnol. Jan. 2009; 27(1): 42-44.*
Zheng and Baum. "Evaluation of promoters for use in tissue-specific gene delivery." Methods Mol Biol. 2008;434:205-19.*
Weeratna et al. "Designing gene therapy vectors: avoiding immune responses by using tissue-specific promoters." Gene Ther. Dec. 2001;8(24):1872-8.*
Ferretti et al. "Role of fractalkine/CX3CL1 and its receptor in the pathogenesis of inflammatory and malignant diseases with emphasis on B cell malignancies." Mediators of inflammation 2014 (2014).*
Morganti et al. "The soluble isoform of CX3CL1 is necessary for neuroprotection in a mouse model of Parkinson's disease." J Neurosci. Oct. 17, 2012;32(42):14592-601.*
Pabon et al. "Fractalkine as a Neuroprotective Therapy in a Model of Parkinson's Disease." 20th annual USF Health Research Day. Presented Feb. 2010. Abstract #B-84. p. 109.*
Otsuni et al. "CX3CL1, a chemokine finely tuned to adhesion: critical roles of the stalk glycosylation and the membrane domain." Biol Open. Nov. 13, 2014;3(12):1173-82. (Year: 2014).*
Rossi et al. "Cloning and characterization of a new type of mouse chemokine." Genomics. Jan. 15, 1998;47(2):163-70. (Year: 1998).*

(Continued)

*Primary Examiner* — Titilayo Moloye
(74) *Attorney, Agent, or Firm* — Quarles & Brady LLP

(57) ABSTRACT

The subject invention pertains to the use of fractalkine (FKN, CX3CL1) and its receptor CX3CR1 for treatment of neuroinflammation and/or neurodegeneration. In one embodiment, the present invention provides a method for treatment of neuroinflammation and/or neurodegenerative diseases, comprising: administering, to cells of a subject in need of such treatment, an adeno-associated virus that comprises a functional fractalkine gene operably linked to transcriptional control elements. In one embodiment, the subject invention is used to treat or ameliorate Parkinson's disease. The present invention can also be used to treat or ameliorate neuroinflammatory and/or neurodegenerative diseases including, but not limited to, Alzheimer's disease, epilepsy, aging, and traumatic brain injury.

3 Claims, 13 Drawing Sheets

Specification includes a Sequence Listing.

(56) References Cited

OTHER PUBLICATIONS

Wang, J. "Bioinformatic analysis of chicken chemokines, chemokine receptors, and toll-like receptor 21." Texas A&M University Press, Texas (2006). pp. 1-96 (Year: 2006).*
Joshi et al. "Quantitative assessment of relationship between sequence similarity and function similarity." BMC genomics, vol. 8, No. 1. (2007), 222 (Year: 2007).*
Kornegay et al. "Widespread muscle expression of an AAV9 human mini-dystrophin vector after intravenous injection in neonatal dystrophin-deficient dogs." Mol Ther. Aug. 2010;18(8):1501-8. (Year: 2010).*
Arruda et al. "Obstacles and future of gene therapy for hemophilia." Expert Opin Orphan Drugs. 2015;3(9):997-1010. (Year: 2015).*
Haurigot et al. "Whole body correction of mucopolysaccharidosis IIIA by intracerebrospinal fluid gene therapy." J Clin Invest. Aug. 1, 2013; 123(8): 3254-3271. (Year: 2013).*
Meucci, O., et al. "Expression of $CX_3CR1$ Chemokine Receptors on Neurons and their Role in Neuronal Survival" PNAS. Jul. 5, 2000. vol. 97:14, pp. 8075-8080. Chicago.
International Search Report in International Application No. PCT/US2012/045158, filed Jun. 30, 2012.
Bachstetter, A. D. et al., Fractalkine and $CX_3CR1$ Regulate Hippocampal Neurogenesis in Adult and Aged Rats, Neurobiology of Aging, 2011, 32:2030-2044, Elsevier Inc.
Bezard, E. et al., A Tale on Animal Models of Parkinson's Disease, Movement Disorders, Jan. 2011, 26(6):993-1002, Wiley Online Library.
Bhaskar, K. et al., Regulation of Tau Pathology by the Microglial Fractalkine Receptor, Neuron, Oct. 7, 2010, 68:19-31, 2010 Elsevier Inc.
Biber, K. et al., Neuronal 'On' and 'Off' Signals Control Microglia, Trends in Neurosciences, 2007, 30(11):596-602, 2007 Elsevier Ltd.
Blasi, E. et al., Immortalization of Murine Microglial Cells by a V-raf/V-myc carrying Retrovirus, Journal of Neuroimmunology, 1990, 27:229-237, 1990 Elsevier Science Publishers B.V.
Borroni, E. M. et al., Chemokine Receptors Intracellular Trafficking, Pharmacology & Therapeutics, 2010, 127:1-8, 2010 Elsevier Inc.
Brochard, V. et al., Infiltration of $CD4^+$ Lymphocytes into the brain contributes to neurodegeneration in a mouse model of Parkinson disease, The Journal of Clinical Investigation, Jan. 2009, 119(1):182-192.
Broux, B. et al., $CX_3CR1$ Drives Cytotoxic $CD4^+CD28^-$ T Cells into the brain of Multiple Sclerosis Patients, Journal of Autoimmunity, 2012, 38:10-19, 2011 Elsevier Ltd.
Cardona, A. E. et al., Control of Microglial Neurotoxicity by the Fractalkine Receptor, Nature Neuroscience, Jul. 2006, 9(7):917-924, 2006 Nature Publishing Group.
Cardona, A. E. et al., Scavenging Roles of Chemokine Receptors: Chemokine Receptor Deficiency is Associated with Increased levels of Ligand in Circulation and Tissues, 2008, pp. 1-33, 2008 American Society of Hematology.
Carty, N. C. et al., Adeno-Associated Viral (AAV) Serotype 5 Vector Mediated Gene Delivery of Endothelin-converting Enzyme Reduces Aβ Deposits in APP + PS1 Transgenic Mice, Molecular Therapy, Sep. 2008, 16(9):1580-1586, The American Society of Gene Therapy.
Carty, N. et al., Convection-Enhanced Delivery and Systemic Mannitol Increase Gene Product Distribution of AAV Vectors 5, 8, and 9 and Increase Gene Product in the Adult Mouse Brain, Journal of Neuroscience Methods, Oct. 2010, 194:144-153, 2010 Elsevier B.V.
Chapman G. A. et al., Fractalkine Cleavage from Neuronal Membranes Represents an Acute Event in the Inflammatory Response to Excitotoxic Brain Damage, The Journal of Neuroscience, 2000, 20:1-5, 2000 Society for Neuroscience.
Chung, Y. C. et al., Fluoxetine prevents MPTP-induced loss of dopaminergic neurons by inhibiting microglial activation, Neuropharmacology, Jan. 2011, 60:963-974, 2011 Elsevier Ltd.
Chung, Y. C. et al., Paroxetine Prevents Loss of Nigrostriatal Dopaminergic Neurons by Inhibiting Brain Inflammation and Oxidative Stress in an Experimental Model of Parkinson's Disease, The Journal of Immunology, 2010, 185:1230-1237, The American Association of Immunologists, Inc.
Croisier, E. et al., Microglial inflammation in the Parkinsonian Substantia Nigra: Relationship to Alpha-Synuclein Deposition, Journal of Neuroinflammation, Jun. 2005, 2(14):1-8, 2005 Croisier et al, licensee BioMed Central Ltd.
Fuhrmann, M. et al., Microglial Cx3cr1 Knockout Prevents Neuron Loss in a Mouse Model of Alzheimer's Disease, Nat Neurosci, Apr. 2010, 13(4):1-6, Nature America, Inc.
Garton, K. J. et al., Tumor Necrosis Factor-α-converting Enzyme (ADAM17) Mediates the Cleavage and Shedding of Fractalkine (CX3CL1), The Journal of Biological Chemistry, Oct. 12, 2001, 276(41):37993-38001, 2001 The American Society for Biochemistry and Molecular Biology, Inc.
Harrison, J. K. et al., Role for Neuronally Derived Fractalkine in Mediating Interactions between Neurons and CX3CR1-expressing microglia, Proc. Natl. Acad. Sci., Sep. 1998, 95:10896-10901, 1998 The National Academy of Sciences.
Hundhausen, C. et al., Regulated Shedding of Transmembrane Chemokines by the Disintegrin and Metalloproteinase 10 Facilitates Detachment of Adherent Leukocytes, The Journal of Immunology, 2007, 178:8064-8072, The American Association of Immunologists, Inc.
Jackson-Lewis, Vernice et al., Time Course and Morphology of Dopaminergic Neuronal Death Caused by the Neurotoxin 1-methyl-4-phenyl-1,2,3,6-tetrahydropyridine, Neurodegeneration, May 1995, 4:257-269, 1995 Academic Press Limited.
Kim, K. W. et al., In Vivo Structure/ Function and Expression Analysis of the $CX_3C$ Chemokine Fractalkine, Sep. 2011, pp. 1-34, 2011 American Society of Hematology.
Kim, Y. S. et al., Microglia, Major Player in the Brain Inflammation: Their Roles in the Pathogenesis of Parkinson's Disease, Experimental and Molecular Medicine, Aug. 2006, 38(4):333-347.
Kremlev, S. G. et al., Interleukin-10 Inhibits Endotoxin-Induced Pro-Inflammatory Cytokines in Microglial Cell Cultures, Journal of Neuroimmunology, Jan. 2005, 162:71-80, 2005 Elsevier B.V.
Lee, S. et al., CX3CR1 Deficiency Alters Microglial Activation and Reduces Beta-Amyloid Deposition in Two Alzheimer's Disease Mouse Models, The American Journal of Pathology, Nov. 2010, 177(5):2549-2562, American Society for Investigative Pathology.
Ludwig, A. et al., Transmembrane Chemokines: Versatile 'Special Agents' in Vascular Inflammation, Thromb Haemost, 2007, 97:694-703, 2007 Schattauer GmbH, Stuttgart.
Lyons, A. et al., Fractalkine-Induced Activation of the Phosphatidylinositol-3 Kinase Pathway Attenuates Microglial Activation in Vivo and in Vitro, Journal of Neurochemistry, 2009, 110:1547-1556, 2009 The Authors Journal Compilation, 2009 International Society for Neurochemistry.
Maciejewski-Lenoir, D. et al., Characterization of Fractalkine in Rat Brain Cells: Migratory and Activation Signals for $CX_3CR$-1-Expressing Microglia, The Journal of Immunology, 1999, 163:1628-1635, The American Association of Immunologists, Inc.
McGeer, P. L., et al., Inflammation and Neurodegeneration in Parkinson's Disease, Parkinsonism and Related Disorders, Jan. 2004, 10:S3-S7, 2004 Elsevier Ltd.
Mizuno, T. et al., Production and Neuroprotective Functions of Fractalkine in the Central Nervous System, Brain Research, Mar. 2003, 979:65-70, 2003 Elsevier B.V.
Mizutani, N. et al., Dose-Dependent Differential Regulation of Cytokine Secretion from Macrophages by Fractalkine, The Journal of Immunology, 2007, 179:7478-7487, 2007 The American Association of Immunologists, Inc.
Neel, N. F. et al., Chemokine Receptor Internalization and Intracellular Trafficking, Cytokine & Growth Factor Reviews, Jul. 2005, 16:637-658, 2005 Elsevier Ltd.
Pabon, M. M. et al., CX3CL1 Reduces Neurotoxicity and Microglial Activation in a Rat Model of Parkinson's Disease, Journal of Neuroinflammation, 2011, 8(9):1-7, 2011 Pabon et al; licensee BioMed Central Ltd.
Przedborski, S. et al., the Parkinsonian Toxin 1-Methyl-4-Phenyl-1,2,3,6-Tetrahydropyridine (MPTP): A Technical Review of its

(56) References Cited

OTHER PUBLICATIONS

Utility and Safety, Journal of Neurochemistry, 2001, 76:1265-1274, 2001 International Society for Neurochemistry.

Ransohoff, R. M. et al., Chemokines and Chemokine Receptors: Multipurpose Players in Neuroinflammation, International Review of Neurobiology, 82:187-204, 2007 Elsevier Inc.

Ré, D. B. et al., Fractalkine: Moving from Chemotaxis to Neuroprotection, Nature Neuroscience, Jul. 2006, 9(7):859-861, 2006 Nature Publishing Group.

Rogers, J. T. et al., CX3CR1 Deficiency Leads to Impairment of Hippocampal Cognitive Function and Synaptic Plasticity, The Journal of Neuroscience, Nov. 9, 2011, 31(45):16241-16250, 2011 The Authors.

Sriram, K. et al., Mice Deficient in TNF Receptors are Protected Against Dopaminergic Neurotoxicity: Implications for Parkinson's Disease, Public Health Resources, 2002, pp. 1-22.

Tieu, K. et al., Nitric Oxide and Reactive Oxygen Species in Parkinson's Disease, Life, Jun. 2003, 55(6):329-335, 2003 IUBMB.

Vroon, A. et al., Neuroinflammation in Parkinson's Patients and MPTP-treated Mice is not Restricted to the Nigrostriatal System: Microgliosis and Differential Expression of Interleukin-1 Receptors in the Olfactory Bulb, Experimental Gerontology, Apr. 2007, 42:762-771, 2007 Elsevier Inc.

Wu, D. C. et al., Blockade of Microglial Activation Is Neuroprotective in the 1-Methyl-4-Phenyl-1,2,3,6-Tetrahydropyridine Mouse Model of Parkinson Disease, the Journal of Neuroscience, Mar. 2002, 22(5):1763-1771, 2002 Society for Neuroscience.

Wu, D. C. et al., NADPH Oxidase Mediates Oxidative Stress in the 1-Methyl-4-Phenyl-1,2,3,6-Tetrahydropyridine Model of Parkinson's Disease, PNAS, May 13, 2003, 100(10):6145-6150.

Wynne, A. M. et al., Protracted Downregulation of $CX_3CR1$ on Microglia of Aged Mice After Lipopolysaccharide Challenge, Brain, Behavior, and Immunity, May 2010, 24:1190-1201, 2010 Elsevier Inc.

Yasuda, Y. et al., The Effects of MPTP on the Activation of Microglia/Astrocytes and Cytokine/Chemokine Levels in Different Mice Strains, Journal of Neuroimmunology, Aug. 2008, 204:43-51, 2008 Elsevier B.V.

Zolotukhin, S. et al., Production and Purification of Serotype 1, 2, and 5 Recombinant Adeno-Associated Viral Vectors, Methods, Jul. 2002, 28:158-167, 2002 Elsevier Science (USA).

Zujovic, V. et al., In Vivo Neutralization of Endogenous Brain Fractalkine Increases Hippocampal TNFα and 8-Isoprostane Production Induced by Intracerebroventricular Injection of LPS, Journal of Neuroimmunology, Jan. 2001, 115:135-143, 2001 Elsevier Science B.V.

Zujovic, V. et al., Fractalkine Modulates TNF-α Secretion and Neurotoxicity Induced by Microglial Activation, GLIA, 2000, 29:305-315, 2000 Wiley-Liss, Inc.

West, M. J. et al., Unbiased Stereological Estimation of the Total Number of Neurons in the Subdivisions of the Rat Hippocampus Using the Optical Fractionator, The Anatomical Record, Mar. 1991, 231:482-497, 1991 Wiley-Liss, Inc.

\* cited by examiner

Native Human amino acid sequence: h1aa - 397aa
Native Mouse amino acid sequence: m1aa - 395aa

```
h-NTN    MAPISLSWLLRLATFCHLTVLLAGQHHGVTKCNITCSKMTSKIPVALLIH  50
m-NTN    MAPSPLAWLLRLAAFFHLCTLLPGQHLGMTKCEIMCDKMTSRIPVALLIR  50
         ***  * ****** *    *  ***  *  *  **  ***** h-NTN    YQQNQASCGKRAITLETRQHRLFCADPKEQWVKDAMQHLDRQAAALTRNG  100
m-NTN    YQLNQESCGKRAIVLETTQHRRFCADPKEKWVQDAMKHLDHQAAALTKNG  100
           **** * **  ***  ** *  **** h-NTN    GTFEKQIGEVKPRTTPAAGGMDESVVLEPE.ATGESSSLEPTPSSQEAQR  149
m-NTN    GXFEKRVDNVTPGITLATRGLSPSALTKPESATLEDLALELTTISQEARG  150
         * ***   *     *  *   *   *        *   ** * **** h-NTN    ALGTSPELPTCVTCSSCTRLPPTPKAQDGG....PVGTELFRVPPVSTAA  195
m-NTN    TMGTSQEPPAAVTGSS....LSTSEAQDAGLTAKPQSIGSFEAADIST.T  195
         *** * * *****       * ***  *   *      ** h-NTN    TWQSSAPHQPGPSLWAEAKTSEAPSTQDPSTQASTASSPAPEENAPSEGQ  245
m-NTN    VWPSPAVYQSGSSSWAEEKATESPSTTAPSPQVSTTSPSTPEENVGSEGQ  245
          *  *   *  *  * *** *   * ***   *  **  * ** ** h-NTN    RVWGQGQSPRPENSLEREEMGPVPAHTDAFQDWGPGSMAHVSVVPVSSEG  295
m-NTN    PPWVQGQDLSPEKSLGSEEINPV..HTDNFQERGPGNTVHPSVAPISSEE  293
          * *           *  *   * **  * *** h-NTN    TPSREPVASGSWTPKAEEPIHATMDPQRLGVLITPVPDAQAATRRQAVGL  345
m-NTN    TPSPELVASGSQAPKIEEPIHATADPQKLSVLITPVPDTQAATRRQAVGL  343
         *** * ***    ***** *  ********** ****** h-NTN    LAFLGLLFCLGVAMFTYQSLQGCPRKMAGEMAEGLRYIPRSCGSNSYVLV  395
m-NTN    LAFLGLLFCLGVAMFAYQSLQGCPRKMAGEMVEGLRYVPRSCGSNSYVLV  393
         ************* ***********  ********** h-NTN    PV  397
m-NTN    PV  395
         **
```

FIG. 4

Mutant Human amino acid sequence: h1aa – 397aa (changed R339-R340 to A339-A340)

Mutant Mouse amino acid sequence: m1aa – 395 aa (changed R337-R338 to A337-A338)

```
h-NTN    MAPISLSWLLRLATFCHLTVLLAGQHEGVTKCNITCSKMTSKIPVALLIH  50
m-NTN    MAPSPLAWLLRLAAFFHLCTLLPGQRLGMTKCEIMCDKMTSRIPVALLIR  50
         ***  * ****** *    *** * *** * * ** ***** h-NTN    YQQNQASCGKRAITLETRQHRLFCADPKEQWVKDAMQHLDRQAAALTRNG  100
m-NTN    YQLNQESCGKRAIVLETTQHRRFCADPKEKWVQDAMKHLDHQAAALTKNG  100
           ****   * *****   * * **** h-NTN    GTFEKQICEVKPRTTPAAGGMDESVVLEPR.ATGBSSSLEPTPSSQEAQR  149
m-NTN    GKPEKRVDNVTPGITLATRQLSPSALTKPESATLEDLALELTTISQEARG  150
         *  ***   *  * *  *   *     *   **  *  **** h-NTN    ALGTSFELPTGVTGSSGTRLPPTPKAQDGG....PVGTELPRVPPVGTAA  195
m-NTN    TMGTEQEPPAAVTGSS....LSTSEAQDAGLTAKPQSIGSPEAADIST.T  195
          *** *  ***** *    * ***  *    *   *    ** h-NTN    TWQSSAPHQPGPSLWAEAKTSEAPSTQDPSTQASTAGSPAPERNAPSEGQ  245
m-NTN    VWPSPAVYQSGSSSWAEEKATESPSTTAPSPQVSTTSPSTPKENVGSEGQ  245
          * *   *     * * *  ** * ** *     ** h-NTN    RVWGQGQSPRPENSLEREEXGFVPAHTDAPQDWGPGSMAHVSVVPVSSEG  295
m-NTN    PPWVQGQDLSPSKSLGSSEINPV..RTDNFQERGPGNTVHPSVAPTSSSS  293
          * *       ** *   *   *** * ** * *** h-NTN    TPSREPVASGSWTPKARRPIHATMDPQRLGVLITPVPDAQAATRROAVGL  345
m-NTN    TPSPELVASGSQAPKIERPINATADPQKLSVLITPVPDTQAATRROAVGL  343
         ***  * ****      *** * ****** * *** h-NTN    LAFLGLLFCLGVAMPTYQSLQGCPRKMAGEMAEGLRYIPRSCGSNSYVLV  395
m-NTN    LAFLGLLFCLGVAMPAYQSLQGCPRKMAGEMVEGLRYVPRSCGSNSYVLV  393
         *************  ************   ************* h-NTN    PV  397
m-NTN    PV  395
         **
```

FIG. 5

Soluble Human amino acid sequence: h1aa - 338aa

Soluble Mouse amino acid sequence: m1aa - 336aa

```
h-NTN    MAPISLSWLLRLATFCHLTVLLAGQHHGVTKCNITCSKMTSKIPVALLIH  50
m-NTN    MAPSPLAWLLRLAAFFHLCTLLPGQHLGMTKCEIMCDKMTSRIPVALLIR  50
         ***  * ****** *    *** * *** * * ** ***** h-NTN    YQQNQASCGKRAIILETRQHRLFCADPKEQWVKDAMQHLDRQAAALTRNG 100
m-NTN    YQLNQESCGKRAIVLETTQHRRFCADPKEKWVQDAMKHLDHQAAALTKNG 100
           ***** * * ***  * * **** h-NTN    GTFEKQIGEVKPRTTPAAGGMDESVVLEPE.ATGESSSLEPTPSSQEAQR 149
m-NTN    GKFEKRVDNVTPGITLATRGLSFSALTKPESATLEDLALELTTISQEARG 150
         * ***    *  *   *  *      *        *  ** * **** h-NTN    ALGTSPELPTCVTGSSGTRLPPTPKAQDGG....PVGTELFRVPPVSTAA 195
m-NTN    TMGTSQEPPAAVTGSS....LSTSEAQDAGLTAKPQSIGSFEAADIST.T 195
         *** * *    ****      * *** *    *      *       ** h-NTN    TWQSSAPHQPGPSLWAEAKTSEAPSTQDPSTQASTASSPAPEENAPSEGQ 245
m-NTN    VWPSPAVYQSGSSSWAEEKATESPSTTAPSPQVSTTSPSTPEENVGSEGQ 245
         * *  *  *   * * *  * *** *       ** h-NTN    RVWGQGQSPRPENSLEREEMGPVPAHTDAFQDWGPGSMAHVSVVPVSSEG 295
m-NTN    PPWVQGQDLSPEKSLGSEEINPV..HTDNFQERGPGNTVHPSVAPISSEE 293
         * *        *  *   ** * *** h-NTN    TPSREPVASGSWTPKAEEPIHATMDPQRLGVLITPVPDAQAAT       338
m-NTN    TPSPELVASGSQAPKIEEPIHATADPQKLSVLITPVPDTQAAT       336
         *** * ***** ** ******* *** * ******* ********
```

FIG. 6

RECOMBINANT ADENO-ASSOCIATED VIRUS-MEDIATED EXPRESSION OF FRACTALKINE FOR TREATMENT OF NEUROINFLAMMATORY AND NEURODEGENERATIVE DISEASES

CROSS-REFERENCE TO RELATED APPLICATION

This application is the U.S. national stage application of International Patent Application No. PCT/US2012/045158, filed Jun. 30, 2012, which claims the benefit of U.S. provisional application Ser. No. 61/503,958, filed Jul. 1, 2011, which are herein incorporated by reference in their entirety.

BACKGROUND OF THE INVENTION

Parkinson's disease (PD) is a disabling, progressive neurodegenerative disorder. Major symptoms of PD include disturbance of the motor system, in which motor coordination and speed become impaired, muscles become rigid, and uncontrollable twitching of groups of muscles produces tremor. The symptoms of PD are primarily caused by a progressive loss of dopaminergic neurons within the pars compacta of the substantia nigra (SNpc). The degeneration of dopaminergic neurons decreases the levels of the neurotransmitter dopamine in the nigrostriatal system.

Neuroinflammation may also play a role in the degeneration of nigrostriatal pathway and the progression of PD pathology. For example, changes in synaptic transmission, axonal transport and increased inflammation precede α-synuclein-mediated neuronal death in neruodegenerative diseases such as Parkinson's disease. Under normal conditions, microglia protect the central nervous system (CNS) function and remove cells damaged from acute injury. However, microglial neurotoxicity can occur after excessive and uncontrolled stimulation or when microglia function is impaired. Microglia can cause neuronal damage through uncontrolled production of pro-inflammatory molecules, such as pro-inflammatory cytokines, reactive oxygen species (ROS), and nitric oxide (NO). Microglia activation also represents a hallmark of other neurological disorders including, but not limited to, Alzheimer's disease, epilepsy, aging, and traumatic brain injury.

Fractalkine (FKN, CX3CL1) is a chemokine constitutively expressed by healthy neurons and its receptor CX3CR1 in microglia. FKN can control the activation of microglia by maintaining microglia in the resting state. FKN can also modulate the over-production of pro-inflammatory modules such as iNOS, IL1β, TNFα and IL-6 by microglia. Therefore, FKN acts as an important endogenous anti-inflammatory modulator during neuronal injury.

The native form of FKN (nFKN) is a transmembrane protein. The membrane-bound form, consisting of an intracellular domain and a transmembrane domain, displays adhesion properties. The soluble FKN form (sFKN) results from the cleavage of the membrane-bound nFKN by ADAM10/17 and/or cathepsin S. It is suggested that, in response to insults, the membrane-bound nFKN is cleaved into the sFKN form (Chapman et al. (2000)). sFKN has been shown to be both neuroprotective and neurodegenerative. It is suggested that sFKN is important for chemotaxis, whereas the membrane-bound nFKN is important for adhesion of monocytes to endothelial cells in the periphery. Different forms of FKN also elicit different immune responses.

CX3CR1, the only receptor for FKN, has been reported as necessary for cell death in a mouse model of AD (Fuhrmann et al. (2000)); however, the loss of CX3CR1 has also shown to exacerbate neurodegeneration. It is reported that mice null for the FKN receptor (CX3CR1−/−) show markedly increased cytokine activation in response to the inflammatory reagent lipopolysacharide (LPS) and a subsequent increase in neuronal cell death. In a toxic model of PD (treated with the neurotoxin MPTP), CX3CR1 knock outs showed more extensive neuron loss than littermate controls. Specifically, CX3CR1−/− mice exhibited an increased classical activation state with higher levels of IL-1β and TNFα, which resulted in increased neurotoxicity. A cross between CX3CR1−/− mice and APP/PS1 mice was shown to result in a decrease in Aβ, yet a cross between CX3CR1−/− mice with a human tau mouse resulted in an increase in tau pathology. CX3CR1−/− mice also show increased susceptibility to neurotoxins such as MPTP, probably due to an increased M1/classical activation state of microglia.

While a complete loss of FKN signaling can lead to microglia-mediated neuronal injury and death, it is unclear whether supraphysiological levels of FKN would be neuroprotective. It also remains unclear whether different forms of FKN (e.g. nNFK and sNFK) would produce the same or different therapeutic effects. As will be clear from the disclosure that follows, these and other benefits are provided by the subject invention.

BRIEF SUMMARY OF THE INVENTION

The present invention provides rAAV-fractalkine constructs and uses thereof for treatment of neuroinflammatory and neurodegenerative diseases. In one embodiment, the present invention provides a recombinant adenovirus-associated viral construct comprising a nucleic acid molecule encoding a fractalkine peptide operably linked to a promoter and/or other transcriptional control elements. In one embodiment, increased fractalkine expression is achieved in the central nervous system, or more specifically, in the brain region of a subject having a neuroinflammatory and neurodegenerative disease.

In another embodiment, the present invention provides a method for treatment of neuroinflammatory and/or neurodegenerative diseases, comprising: administering, into cells of a subject in need of such treatment, an effective amount of a pharmaceutical composition comprising a rAAV vector that comprises a nucleic acid molecule encoding a fractalkine peptide operably linked to a promoter and/or transcriptional control elements. In one embodiment, the subject invention is used to treat or ameliorate Parkinson's disease.

In certain embodiments, the fractalkine peptide in accordance with the present invention is a soluble isoform of the fractalkine peptide (sFKN) or a fractalkine peptide that can be endogenously cleaved into a soluble isoform (such as the native form).

Also provided is the use of FKN receptor (CX3CR1) agonists for treatment or amelioration of neuroinflammatory and neurodegenerative diseases. In one embodiment, the administration of FKN receptor (CX3CR1) agonists can be used to prevent and/or reduce synuclein nigral neuron loss.

BRIEF DESCRIPTION OF THE DRAWINGS

FIG. 4 shows alignment amino acid sequences of a native form of human FKN (SEQ ID NO:9) and a native form of mouse FKN (SEQ ID NO:6).

FIG. 5 shows alignment amino acid sequences of a mutant membrane-bound form of human FKN (SEQ ID NO:11) and a mutant membrane-bound form of mouse FKN (SEQ ID NO:8).

FIG. 6 shows alignment amino acid sequences of a soluble form of human FKN (SEQ ID NO:10) and a soluble form of mouse FKN (SEQ ID NO:7).

BRIEF DESCRIPTION OF THE SEQUENCES

Figure 1:
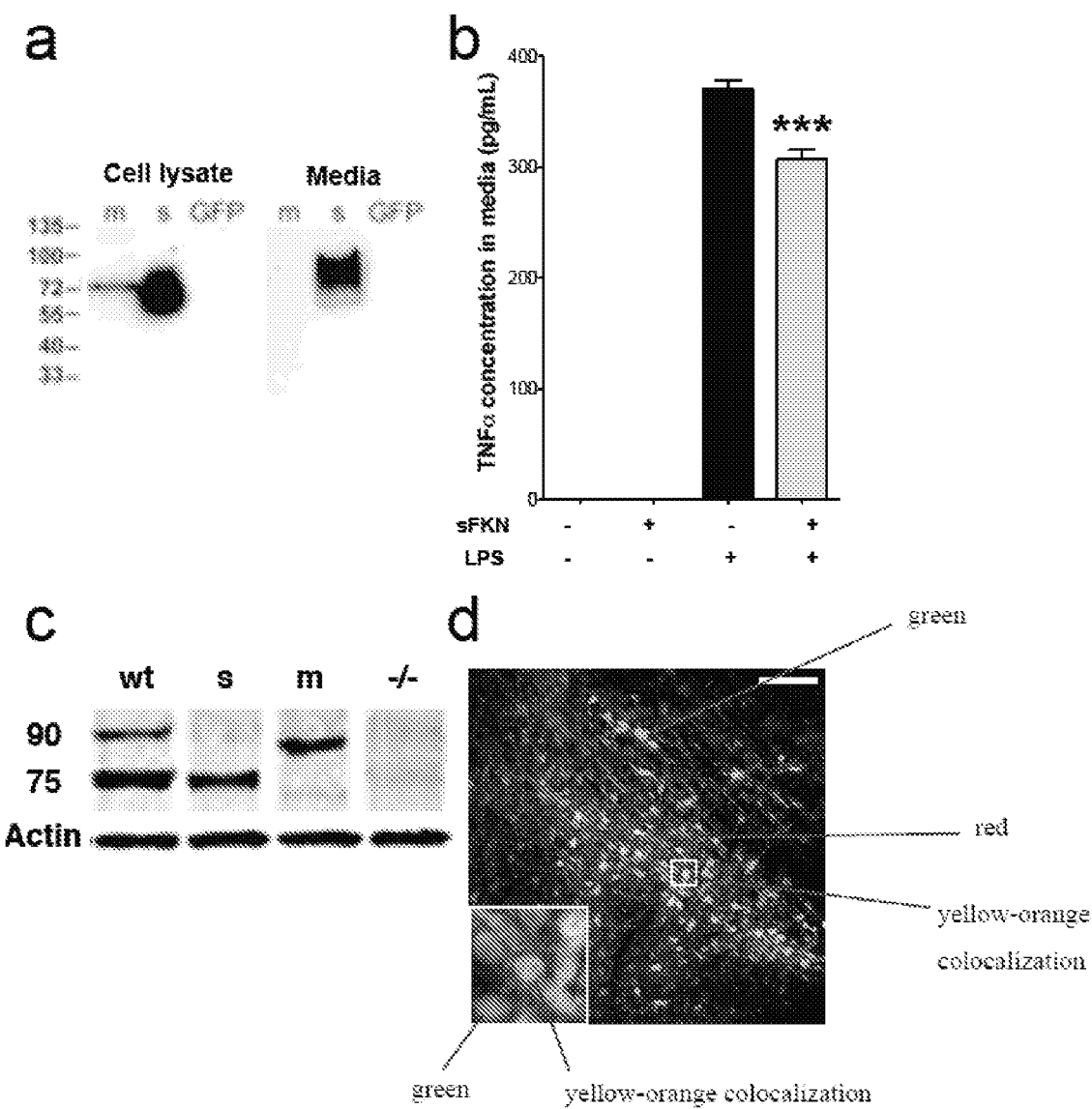
FIG. 1 relates to the generation and validation of rAAV-FKN constructs. (A) Western blot analysis of sFKN (s), mFKN (m), and GFP expressed in HEK293 cells using an anti-hemagglutinin antibody. Only the sFKN isoform is detected in the media, while both the sFKN isoform and the mFKN isoform are found in the crude cell lysate. (B) ELISA quantification of TNFα secreted from BV2 cells. Pre-treatment with sFKN conditioned media attenuates (***p<0.05) the secretion of TNFα from BV2 cells, when exposed to 100 ng of LPS for 4 hrs. sFKN conditioned media alone does not induce the secretion of TNFα. (C) Western blot analysis of in vivo expression of wild type (wt), sFKN (s), mFKN (m), and CX3CL1$^{-/-}$ (−/−) tissue lysates using an anti-CX3CL1 antibody. Both sFKN (s) and mFKN (m) produce a single band consistent with the molecular weight of each isoform reported in the literatures and relative to that of WT. mFKN (m) yields a single band indicating that constitutive proteolytic cleavage by ADAM10/17 is abated. (D) In vivo expression pattern of rAAV-GFP (the rAAV-GFP vector comprises the same promoter as the rAAV-FKN vectors). Delivery of the rAAV-GFP vector to the SNpc results in transduction of neurons of the SN. Green is GFP, red are TH$^+$ neurons, yellow-orange are co-localized expression. Scale bar is 200 μm. Data are presented as mean±SEM.

SEQ ID NO:1 is a nucleic acid sequence of a primer useful according to the present invention.

SEQ ID NO:2 is a nucleic acid sequence of a primer useful according to the present invention.

SEQ ID NO:3 is a nucleic acid sequence of a primer useful according to the present invention.

SEQ ID NO:4 is a nucleic acid sequence of a primer useful according to the present invention.

SEQ ID NO:5 is a nucleic acid sequence of a primer useful according to the present invention.

SEQ ID NO:6 is an amino acid sequence of a native form of mouse FKN (nFKN) peptide useful according to the present invention.

SEQ ID NO:7 is an amino acid sequence of a soluble form of mouse FKN (sFKN) peptide useful according to the present invention.

SEQ ID NO:8 is an amino acid sequence of a mutant membrane-bound form of mouse FKN (mFKN) peptide useful according to the present invention.

SEQ ID NO:9 is an amino acid sequence of a native form of human FKN (nFKN) peptide useful according to the present invention.

SEQ ID NO:10 is an amino acid sequence of a soluble form of human FKN (sFKN) peptide useful according to the present invention.

SEQ ID NO:11 is an amino acid sequence of a mutant membrane-bound form of human FKN (mFKN) peptide useful according to the present invention.

DETAILED DISCLOSURE OF THE INVENTION

The present invention is based on the surprising discovery that neuroinflammatory and neurodegenerative diseases can be treated by increasing fractalkine (FKN, also referred to as CX3CL1) expression in neuronal cells and/or astrocytes. In one embodiment, nigral neuron loss can be prevented or reduced (inhibited) by delivering a therapeutically effective amount of fractalkine to degenerating neurons and/or astrocytes using gene therapy.

In one embodiment, recombinant adeno-associated virus (rAAV) vector comprising a nucleic acid molecule encoding an FKN peptide is administered to neuronal cells. In one embodiment, rAAV vectors comprising a nucleic acid molecule encoding an FKN peptide is administered to degenerating neuronal cells. In one embodiment, rAAV vectors comprising a nucleic acid molecule encoding an FKN peptide is administered to astrocytes. In one embodiment, increased fractalkine expression is achieved in the central nervous system, or more specifically, in the brain region of a subject having a neuroinflammatory and/or neurodegenerative disease.

In one embodiment, increasing fractalkine (FKN) expression in neuronal cells using recombinant adeno-associated virus-mediated gene transfer can be used to reduce pro-inflammatory response in PD and to produce neuroprotective effects on dopaminergic neurons. Specifically, it is discovered that FKN has neuroprotective effects in different models of PD. Specifically, FKN peptide inhibits neuron loss and reduces microglial activation in a 6-OHDA PD model. In this model, FKN reduced microglial activation, and produced significant neuroprotective effects against both TH neuron loss and the lesion volume in the striatum. In addition, the delivery of FKN into neuronal cells using gene therapy (such as recombinant adeno-associated virus (rAAV)-mediated gene therapy), decreased neuron loss in an MPTP mouse model. Increased expression of FKN in neuronal cells also produces neuroprotective effects in an α-synuclein (α-syn) animal model.

Recombinant AAV-Fractalkine Constructs

One aspect of the invention provides a recombinant adenovirus-associated viral construct comprising a nucleic acid molecule encoding an FKN peptide operably linked to a promoter and/or other transcriptional control elements. In one embodiment, the present invention provides recombinant adeno-associated virus (rAAV) virion comprising a rAAV vector for delivery into neuronal cells of a subject, wherein the rAAV vector comprises a nucleic acid molecule encoding an FKN peptide selected from a secreted/soluble form of FKN (sFKN), a native form of FKN (nFKN), and a mutant membrane-bound form (mFKN). In preferred embodiments, the rAAV vector of the present invention comprises a nucleic acid molecule encoding a soluble isoform of a fractalkine peptide (sFKN) or a nucleic acid molecule encoding a fractalkine peptide that can be endogenously cleaved into a soluble isoform (such as the native form). In one embodiment, the nucleic acid molecule encoding an FKN peptide is under the control of an astrocyte-specific promoter such as a GFAP promoter. In one embodiment, the nucleic acid molecule encoding an FKN peptide is under the control of a neuronal-specific promoter. In one embodiment, the rAAV vector is derived from AAV1, AAV2, AAV3, AAV4, AAV5, AAV6, AAV7, AAV8, AAV9, AAV10, or AAV11. In certain specific embodiments, the rAAV vector is derived from AAV2 or AAV9. In one embodiment, the nucleic acid molecule encoding an FKN peptide is under the control of an astrocyte-specific promoter, such as a GFAP promoter. In one embodiment, the nucleic acid molecule encoding an FKN peptide is under the control of a neuron-specific promoter, such as a hybrid CMV-chicken beta-actin promoter.

Adenoviruses have been used as vectors gene therapy. For instance, adenoviral vectors have been used for the cloning and expression of genes in vitro (Gluzman et al., Cold Spring Harbor, N.Y. 11724, p. 187), for the transfer of genes into cells ex vivo (WO95/14785; WO95/06120), or for the transfer of genes into cells in vivo (see WO93/19191, WO94/24297, WO94/08026).

Recombinant adenovirus vectors, constructs derived from AAV viruses, and methods of preparation are known in the art. Preferably, the viral genome is modified so that the virus is incapable of autonomously replicating in the infected cells. As a result, the adenovirus constructs are defective for certain regions of their genome which are essential for replication. For instance, adenovirus vectors used in gene therapy can contain a deletion in/of the E1 region, which is essential for viral replication, or a deletion of another region essential for the viral replication and/or propagation, such as the E4 region. Adenoviral vectors in which the E1 and E4 regions are deleted have highly reduced transcription background noise and viral gene expression. Such vectors have been described, for example, in applications WO94/28152, WO95/02697, WO96/22378. Moreover, vectors carrying a modification at the level of the IVa2 gene has also been described (WO96/10088). In addition, AAV vectors generally lack the entire coding regions Rep and Cap, which are replaced by nucleic acids of interest.

Treatment of Neuroinflammation and Neurodegeneration

Another aspect of the invention provides a method for inhibition and/or treatment of neuroinflammation and/or neurodegenerative diseases by increasing fractalkine expression level. In one embodiment, the method comprises: administering, to a subject in need of such treatment, an effective amount of a pharmaceutical composition comprising a fractalkine peptide and/or a nucleic acid molecule encoding a fractalkine peptide.

In one embodiment, the invention provides a method for inhibition and/or treatment of neuroinflammation and/or neurodegenerative diseases by increasing fractalkine expression level via gene therapy. In one embodiment, the method comprises: administering, into cells of a subject in need of such treatment, a rAAV vector that comprises a nucleic acid molecule encoding a fractalkine peptide operably linked to a promoter and/or transcriptional control elements. In another embodiment, the present invention comprises: administering, into cells of a subject in need of such treatment, a rAAV virion comprising a rAAV vector that comprises a nucleic acid molecule encoding a operably linked to a promoter and/or transcriptional control elements. In one embodiment, the subject invention is used to treat or ameliorate Parkinson's disease.

In certain embodiments, the fractalkine peptide useful for the present invention is a soluble isoform of the fractalkine peptide (sFKN) or a fractalkine peptide that can be endogenously cleaved into a soluble isoform (such as the native form).

In one embodiment, the present invention can be used to treat or ameliorate a neuroinflammatory and/or neurodegenerative disease selected from Parkinson's disease, Alzheimer's disease, epilepsy, aging, traumatic brain injury, multiple sclerosis, dementia, or cortico-basal degeneration. In one specific embodiment, the present invention can be used to treat or ameliorate Parkinson's disease or PD-related disorders, Parkinsonism syndromes or Parkinsonism-plus diseases, including cortical-basal ganglionic degeneration, dementia syndromes (Alzheimer's diases, diffuse Lewy body disease, frontotemporal dementia), Lytico-Bodig (Guamanian Parkinsonism-dementia-ALS), multiple system atrophy syndromes (striatonigral degeneration, Shy-Drager syndrome, sporadic olivopontocerebellar degeneration (OPAC), motor neuron disease parkinsonism), and/or progressive pallidal atrophy.

In one embodiment, the rAAV vector or rAAV virion comprises a nucleic acid molecule encoding an FKN peptide selected from a soluble form of FKN (sFKN), a native form of FKN (nFKN), or a mutant membrane-bound form (mFKN). Preferably, the rAAV vector or rAAV virion comprises a nucleic acid molecule encoding an FKN peptide selected from a soluble form of FKN (sFKN) or a native form of FKN (nFKN). In one embodiment, the rAAV vector or rAAV virion comprises a nucleic acid molecule encoding an FKN peptide comprising a sequence selected from any of SEQ ID NOs: 6-11. In preferred embodiments, the rAAV vector or rAAV virion comprises a nucleic acid molecule encoding an FKN peptide comprising a sequence selected from any of SEQ ID NOs 6, 7, 9, or 10. In one embodiment, the rAAV vector or rAAV virion comprises a nucleic acid molecule encoding an FKN peptide having at least 80%, 85%, 90%, 93%, 95%, 96%, 97%, 98% or 99% identity with any of SEQ ID NOs: 6-11. In preferred embodiments, the rAAV vector or rAAV virion comprises a nucleic acid molecule encoding an FKN peptide having at least 80%, 85%, 90%, 93%, 95%, 96%, 97%, 98% or 99% identity with any of SEQ ID NOs 6, 7, 9, or 10. The term "the fractalkine (FKN) peptide," as used herein, refers to the chemokine that binds CX3CR1. See, e.g., Fong et al. *J. Biol. Chem.* 275: 3781-3786 (2000); Imai et al., *Cell* 91(4):521-30 (1997). Exemplary fractalkine polypeptides include, e.g., SEQ ID NOs: 6, 7, 9, and 10. The amino acid sequences of the native form and the soluble/secreted isoform of the fractalkine (FKN) peptide are publically available and can be readily obtained by a person skilled in the art via databases such as GenBank. Preferably, the fractalkine peptide is of mammalian origin, more preferably, human origin.

Desired amino acid substitutions (whether conservative or non-conservative) can be determined by those skilled in the art at the time such substitutions are desired. In certain embodiments, conservative amino acid substitutions also encompass non-naturally occurring amino acid residues which are typically incorporated by chemical peptide synthesis rather than by synthesis in biological systems. In preferred embodiments, the modified FKN peptides can still be endogenously cleaved into the soluble FKN isoform.

Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

In one embodiment, the adeno-associated virus comprising an FKN gene is administered to cells in the brain, such as substantia nigra, striatum, and hippocampus. In one embodiment, the adeno-associated virus comprising an FKN gene is administered to degenerating neuronal cells. In one embodiment, the adeno-associated virus comprising an FKN gene is administered to astrocytes. In one embodiment, multiple rAAv vectors are delivered via a single injection.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition, chance of re-occurrence or returning of a disease after a remission. In one embodiment, the term "treatment" includes reduces or affects the progression of microgalia activation, neuroinflammation, and/or neurodegeneration. In one specific embodiment, the term "treatment" includes (i) ameliorating a symptom associated with PD or PD-related disorders in a patient diagnosed with PD or PD-related disorders; and/or (ii) relieving (such as attenuate the progress of) or remedying PD or PD-related disorders in a patient diagnosed with PD or PD-related disorders.

The term "prevention" or any grammatical variation thereof (e.g., prevent, preventing, and prevention etc.), as used herein, includes but is not limited to, delaying the onset of symptoms, preventing relapse to a disease, decreasing the number or frequency of relapse episodes, increasing latency between symptomatic episodes, or a combination thereof.

The term "effective amount," as used herein, refers to an amount that is capable of preventing, treating, or ameliorating a disease or condition or otherwise capable of producing an intended therapeutic effect. In certain embodiments, the effective amount enables a 5%, 25%, 50%, 75%, 90%, 95%, 99% and 100% increase in FKN expression. In certain embodiments, the effective amount enables a 5%, 25%, 50%, 75%, 90%, 95%, 99% and 100% reduction in the level of one or more pro-inflammatory biomarkers (e.g., iNOS, IL1β, TNFα, IL-6, and IGF-1) released by microglia.

The term "subject," as used herein, describes an organism, including mammals such as primates, to which treatment with the compositions according to the subject invention can be administered. Mammalian species that can benefit from the disclosed methods include, but are not limited to, apes, chimpanzees, orangutans, humans, monkeys; and other animals such as dogs, cats, horses, cattle, pigs, sheep, goats, chickens, mice, rats, guinea pigs, and hamsters. Typically, the subject is a human.

In one embodiment, FKN is administered, via gene therapy, to a subject who has symptoms of neuroinflammation and/or neurodegeneration, or is diagnosed with a neuroinflammatory and/or neurodegenerative disease. In one embodiment, FKN is administered, via gene therapy, to a subject who is diagnosed of a neurological disease selected from Parkinson's disease, Alzheimer's disease, epilepsy, aging, traumatic brain injury, multiple sclerosis, dementia, or cortico-basal degeneration.

In one specific embodiment, FKN is administered, via gene therapy, to a subject who is diagnosed of Parkinson's disease or PD-related disorders, Parkinsonism syndromes or Parkinsonism-plus diseases, including cortical-basal ganglionic degeneration, dementia syndromes (Alzheimer's diases, diffuse Lewy body disease, frontotemporal dementia), Lytico-Bodig (Guamanian Parkinsonism-dementia-ALS), multiple system atrophy syndromes (striatonigral degeneration, Shy-Drager syndrome, sporadic olivopontocerebellar degeneration (OPAC), motor neuron disease parkinsonism), and/or progressive pallidal atrophy.

A further aspect of the invention relates to the use of FKN receptor (CX3CR1) agonists for treatment or amelioration of neuroinflammation and neurodegenerative diseases. In one embodiment, the administration of FKN receptor (CX3CR1) agonists can be used to prevent and/or reduce synuclein nigral neuron loss. In one embodiment, the present invention provides a method for screening for therapeutic agents that can be used to treat or ameliorate neuroinflammation and neurodegenerative diseases. In one specific embodiment, the candidate agent is an FKN receptor (CX3CR1) agonist. In another specific embodiment, the candidate agent is an enzyme that cleaves the native FKN peptide into a soluable form of FKN peptide.

As used herein, the term "CX3CR1" refers to the receptor of the CX3CL1 (FKN) chemokine. CX3CR1 is encoded by the CX3CR1 gene, which is located at human chromosome location 3p21.3 (Entrez GeneID: 1524). The amino acid sequences of the CX3 CR1 are publically available and can be readily obtained by a person skilled in the art via databases such as GenBank. Preferably, the CX3CR1 is of mammalian origin, more preferably, human origin. In one embodiment, the CX3CR1 useful in accordance of the invention has an amino acid sequence shown in GenBank Accession No. P49238. In one embodiment, the present invention provides treating neuroinflammation and/or neurodegenerative diseases, wherein the method comprises administering, to a subject in need of such treatment, an effective amount of a pharmaceutical composition comprising an agonist of CX3CR1. In one embodiment, the agonist of CX3CR1 is a peptide. In another embodiment, the method comprises administering, to a subject in need of such treatment, the pharmaceutical composition comprises a nucleic acid molecule encoding a peptide agonist of CX3CR1, formulated with pharmaceutically acceptable carriers.

Agonists of CX3CR1 are known in the art, see U.S. Patent Application Publication No. 20120141538, the contents of which are hereby incorporated by reference in its entireties. Agonists of CX3CR1 can be obtained by a person skilled in the art. See U.S. Patent Application Publication No. 20120141538.

Pharmaceutical Compositions

The present invention also provides therapeutic or pharmaceutical compositions comprising the active ingredient in a form that can be combined with a therapeutically or pharmaceutically acceptable carrier. The genetic constructs of the present invention may be prepared in a variety of compositions, and may also be formulated in appropriate pharmaceutical vehicles for administration to human or animal subjects.

The rAAV molecules of the present invention and compositions comprising them provide new and useful therapeutics for the treatment, control, and amelioration of symptoms of a variety of disorders, and in particular, articular diseases, disorders, and dysfunctions, including for example osteoarthritis, rheumatoid arthritis, and related disorders.

The invention also provides compositions comprising one or more of the disclosed rAAV vectors, expression systems, virions, viral particles; or mammalian cells. As described hereinbelow, such compositions may further comprise a pharmaceutical excipient, buffer, or diluent, and may be formulated for administration to an animal, and particularly a human being. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof.

In one embodiment, the number of rAAV vector and/or virion particles administered to a mammal may be on the order ranging from $10^3$ to $10^{13}$ particles/ml, or any values therebetween, such as for example, about $10^7$, $10^8$, $10^9$, $10^{10}$, $10^{11}$, $10^{12}$, or $10^{13}$ particles/ml.

In one embodiment, rAAV vector and/or virion particles of higher than $10^{13}$ particles/ml are be administered. The rAAV vectors and/or virions can be administered as a single dose, or divided into two or more administrations as may be required to achieve therapy of the particular disease or disorder being treated. In most rAAV-based gene therapy regimens, the inventors believe that a lower titer of infectious particles will be required when using the modified-capsid rAAV vectors, than compared to conventional gene therapy protocols.

In certain embodiments, the present invention concerns formulation of one or more rAAV-based compositions disclosed herein in pharmaceutically acceptable solutions for administration to a cell or an animal, either alone or in combination with one or more other modalities of therapy, and in particular, for therapy of human cells, tissues, and diseases affecting man.

If desired, nucleic acid segments, RNA, DNA or PNA compositions that express one or more of therapeutic gene products may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV-based genetic compositions may thus be delivered along with various other agents as required in the particular instance. Such compositions may be purified from host cells or other biological sources, or alternatively may be chemically synthesized as described herein. Likewise, such compositions may further comprise substituted or derivatized RNA, DNA, siRNA, mRNA, tRNA, ribozyme, catalytic RNA molecules, or PNA compositions and such like.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intra-articular, intramuscular administration and formulation.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound(s) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the AAV vector-based therapeutic constructs in suitably formulated pharmaceutical compositions disclosed herein either subcutaneously, intraocularly, intravitreally, parenterally, subcutaneously, intravenously, intracerebro-ventricularly, intramuscularly, intrathecally, orally, intraperitoneally, by oral or nasal inhalation, or by direct injection to one or more cells, tissues, or organs by direct injection. Solutions of the active compounds as freebase or pharmacologically acceptable salts may be prepared in sterile water and may also suitably mixed with one or more surfactants, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms of the AAV-based viral compositions suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers.

The compositions of the present invention can be administered to the subject being treated by standard routes including, but not limited to, oral, parenteral such as intravenous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active AAV vector-delivered therapeutic polypeptide-encoding DNA fragments in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The AAV vector compositions disclosed herein may also be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

The amount of AAV compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the AAV vector compositions, either over a relatively short, or a relatively prolonged period of time, as may be determined by the medical practitioner overseeing the administration of such compositions.

Expression Vectors

The present invention contemplates a variety of AAV-based expression systems, and vectors. In one embodiment the preferred AAV expression vectors comprise at least a first nucleic acid segment that encodes a therapeutic peptide, protein, or polypeptide.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules.

To express a therapeutic agent in accordance with the present invention one may prepare a tyrosine-modified rAAV expression vector that comprises a therapeutic agent-encoding nucleic acid segment under the control of one or more promoters. To bring a sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded polypeptide. This is the meaning of "recombinant expression" in this context. Particularly preferred recombinant vector constructs are those that comprise a rAAV vector. Such vectors are described in detail herein.

Exemplary promoters for use in the rAAV vectors of the invention include, but are not limited to, viral, mammalian, and avian promoters, including for example a CMV promoter, a beta-actin promoter, a hybrid CMV promoter, a hybrid beta-actin promoter, an EF1 promoter, a U1a promoter, a U1b promoter, a Tet-inducible promoter, a VP16-LexA promoter, and such like.

The vectors or expression systems may also further comprise one or more enhancers, regulatory elements, transcriptional elements, to alter or effect transcription of the heterologous gene cloned in the rAAV vectors. For example, the rAAV vectors of the present invention may further comprise at least a first CMV enhancer, a synthetic enhancer, or a cell- or tissue-specific enhancer. The exogenous polynucleotide may also further comprise one or more intron sequences.

Therapeutic Kits

The invention also encompasses one or more of the genetically-modified rAAV vector compositions described herein together with one or more pharmaceutically-acceptable excipients, carriers, diluents, adjuvants, and/or other components, as may be employed in the formulation of particular rAAV-polynucleotide delivery formulations, and in the preparation of therapeutic agents for administration to a subject, and in particularly, to a human. In particular, such kits may comprise one or more of the disclosed rAAV compositions in combination with instructions for using the viral vector in the treatment of such disorders in a subject, and may typically further include containers prepared for convenient commercial packaging.

The composition may include partially or significantly purified rAAV compositions, either alone, or in combination with one or more additional active ingredients, which may be obtained from natural or recombinant sources, or which may be obtainable naturally or either chemically synthesized, or alternatively produced in vitro from recombinant host cells expressing DNA segments encoding such additional active ingredients.

Therapeutic kits may also be prepared that comprise at least one of the compositions disclosed herein and instructions for using the composition as a therapeutic agent. The container means for such kits may typically comprise at least one vial, test tube, flask, bottle, syringe or other container means, into which the disclosed rAAV composition(s) may be placed, and preferably suitably aliquoted. Where a second therapeutic polypeptide composition is also provided, the kit may also contain a second distinct container means into which this second composition may be placed. Alternatively, the plurality of therapeutic biologically active compositions may be prepared in a single pharmaceutical composition, and may be packaged in a single container means, such as a vial, flask, syringe, bottle, or other suitable single container means. The kits of the present invention will also typically include a means for containing the vial(s) in close confinement for commercial sale, such as, e.g., injection or blow-molded plastic containers into which the desired vial(s) are retained.

In accordance with the present invention, neuroprotective capacity of the soluble and the membrane-bound CX3CL1 isoforms are investigated in a 1-methyl-4-phenyl-1,2,3,6-tetrahydropyridine (MPTP) mouse model of PD. MPTP has been reliably used to induce DA cell loss in the SNpc of mice and non-human primates and the MPTP model is an art-recognized model for Parkinson's disease (Przedborski et al., 2001). To determine the functional significance of the soluble v. the membrane-bound CX3CL1 isoform, recombinant adeno-associated viruses (rAAVs) are constructed to selectively express either the soluble CX3CL1 or a mutant isoform (the mutant form is proteolytically resistant to cleavage and remains membrane-bound). Also, a control vector expressing green fluorescent protein (GFP) is constructed. Each vector is injected into the SNpc of CX3CL1$^{-/-}$ mice such that the only CX3CL1 present in the mice is either solely soluble or membrane-bound.

To examine the ability of the CX3CL1 isoform to dampen the neurotoxic effects of MPTP, common behavioral, immunological, and biochemical assays are conducted. The results show a significant reduction in the classic neurotoxic pathology associated with MPTP exposure in CX3CL1 null mice that received the vector expressing only the soluble isoform. In addition, CX3CL1 null mice, which express only the membrane-bound isoform of CX3CL1 in the SNpc, have exacerbated pathologies akin to CX3CL1 null mice expressing the GFP control vector. The results show that the neuroprotective capacity of CX3CL1 is exclusively reliant on the soluble isoform in an MPTP model of PD.

Disruption of CX3CL1-CX3CR1 signaling in the brain exacerbates MPTP-induced DA neurodegeneration (Cardona et al., 2006). Functionally, this signaling pair has been shown across a variety of studies to dampen microglial activation and subsequent toxicity. Before the present invention, the biological activity of the soluble or the membrane-bound CX3CL1 isoform is unknown. The biological activity of the soluble versus the uncleaved membrane-anchored isoforms of CX3CL1 is examined in the present invention.

The results show that only sFKN isoform attenuates the neurotoxic effects of MPTP on the nigrastriatal network and that the membrane-anchored (mFKN) isoform has no neuroprotective effect on animals treated with MPTP. Treatment with sFKN reduces impairment of motor coordination, prevents exacerbation of DA neuron loss, and ameliorates microglia activation and pro-inflammatory cytokine release, all of which are commonly associated with the MPTP mouse model of PD.

An exogenous truncated peptide of CX3CL1 was able to reduce 6-OHDA associated neurotoxicity in a rat model of PD (Pabon et al., 2011). In this invention, a mutant membrane-bound CX3CL1 isoform is constructed. The mFKN contains a point mutation at the ADAM10/17 cleavage site, thus preventing ADAM10/17 from cleaving the mutant form to product the soluble isoform. Also, by using CX3CL1 null mice, treatment effects of each of the rAAV-sFKN and rAAV-mFKN in response to MPTP can be examined.

In accordance with the present invention, the results show that sFKN attenuates the LPS-induced secretion of TNFα from BV2 cells in vitro. In addition, Western blot analysis shows that in vitro and in vivo expression of rAAV-sFKN and rAAV-mFKN produces the soluble (sFKN) and mutated form (that remains permanently attached to the neuronal membrane (mFKN)), respectively. Following the MPTP and saline injections of rAAV-FKN vectors, all mice are subjected to behavioral analysis to examine motor coordination. As one of the primary pathological hallmarks of PD in humans is motor coordination dysfunction (Bezard and Przedborski, 2011), it is important to examine the effect of the sFKN and mFKN on ameliorating motor coordination impairment. The MPTP induced motor deficit is significantly ameliorated by treatment with sFKN, resembling that of WT-MPTP controls. The full-length CX3CL1 isoform produced by mFKN provides no amelioration of MPTP induced motor impairment.

A pathological hallmark of PD is neurodegeneration in the SNpc leading to a selective loss of DA neurons. The subsequent depletion of DA projections to the striatum leads to impairments in motor coordination. Previous literature has shown an exaggerated response to MPTP in CX3CL1 deficient mice (Cardona et al., 2006), which is also observed in the present invention. A significant reduction of TH in the striatum is observed in MPTP treated mice. Mice expressing sFKN has significantly more TH in the striatum, when compared to mice expressing mFKN or GFP. In addition, there is a significant depletion of the number of TH positive cells in the SNpc in response to MPTP, which is ameliorated by treatment with sFKN. mFKN treated mice have significantly less TH positive neurons compared to sFKN and resemble those treated with rAAV-GFP. Expression of TH has been shown to be somewhat plastic in response to MPTP and therefore a decline in TH is not necessarily an indicative marker of degenerating DA neurons (Jackson-Lewis et al., 1995). To assess whether neuronal loss occurred in mice, the amount of NeuN staining in the SNpc is determined. The neuronal loss associated with MPTP administration shows a trend of recovery by administration of sFKN, while this trend is blunted by either mFKN or mice that lack any CX3CL1 (GFP).

CX3CL1 to CX3CR1 communication is one way that neurons are thought to directly interact with microglia. Several studies have indicated that an acute inflammatory insult such as LPS exposure is sufficient to disrupt this dialog via down regulation of CX3CR1 transcript and protein levels. The results show that exposure to acute administration of MPTP does not affect the signaling capabilities of this pair as both CX3CR1, and CX3CL1 protein levels remain unchanged in response to MPTP exposure. The rAAV-sFKN and the rAAV-mFKN vectors can restore CX3CL1 in CX3CL1 null mice back to the levels seen in WT mice.

The aberrant activation of microglia has been shown to exacerbate the pathophysiology associated with PD. In the current invention, the ability of the soluble and membrane-bound FKN isoform to attenuate the activation of microglia is evaluated in the MPTP model. The results show that sFKN can abrogate the induction of CD68 phagocytic microglia, while mFKN treatment has no effect to reduce this activation state. In addition, the amount of CD11b reactive microglia is markedly reduced in mice that expressed sFKN, when compared to both mFKN and GFP groups. In addition, a truncated CX3CL1 peptide has been shown to reduce the production of multiple pro-inflammatory molecules (Zujovic et al., 2000; Zujovic et al., 2001; Biber et al., 2007; Mizutani et al., 2007) in vitro. The results show that sFKN attenuates the production of both IL-1β and TNFα in the VM of MPTP-injected mice. Furthermore, mice expressing only the membrane-bound form have significantly higher levels of both pro-inflammatory cytokines, presenting an inflammatory phenotype similar to mice expressing the rAAV-GFP. The results indicate that treatment with mFKN do not effectively reduce the histological and molecular pro-inflammatory phenotype in the MPTP model.

In accordance with the present invention, it is discovered that CX3CL1 mediates anti-inflammatory effect of microglia is solely through the soluble isoform, in a MPTP mouse model of PD. In this model, the results show that sFKN ameliorates impaired motor coordination through a reduction in microglia activation and subsequent pro-inflammatory response. The mFKN isoform does not have an effect on reduction of microglia activation and pro-inflammatory responses in MPTP-treated mouse.

Given that only the soluble form of CX3CL1 provides an anti-inflammatory and neuroprotective function in the MPTP model of PD, it is postulated that ligation with the soluble isoform, but not the membrane-bound isoform, allows for CX3CR1 internalization. Recent literature has indicated that multiple chemokine receptors actively retreat through internalization to the cytoplasm following ligation to affect downstream signaling pathways (Neel et al., 2005; Borroni et al., 2010). The anti-inflammatory capacity of CX3CL1 in the CNS is only observed with the use of the soluble isoform, it is also postulated that CX3CR1 internalization is a functional aspect of this signaling system. Although ligation of mFKN with CX3CR1 is possible through the chemokine domain, the permanent attachment of CX3CR1 to the membrane may prevent subsequent internalization to the cytoplasm of microglia, thereby altering any downstream effectors. Therefore, it is postulated that only the soluble domain of CX3CL1 can be readily internalized with CX3CR1 ligation. Recent literature corroborates this hypothesis in that CX3CR1 actively removes soluble CX3CL1 from the surrounding milieu, as CX3CR1$^{-/-}$ mice have substantially more circulating CX3CL1 (Cardona et al., 2008). The fact that the soluble CX3CL1 isoform is internalized with CX3CR1 ligation is consistent with the need for the constitutive and endogenous proteolytic cleavage by ADAM10/17 to yield soluble CX3CL1 in an effort to maintain a constant neuroprotective dialog between neurons and microglia.

Materials and Methods

AAV Production rAAV9 constructs expressing the two different forms of CX3CL1 (GenBank Accession No. NM_009142 version GI:114431260) were cloned using PCR from mouse brain cDNA. The soluble form (sFKN; αα 1-336) was generated with primers Frac5' (GAGACCGGTCCACCATGGCTC-CCTCGCCGCTCGCG) (SEQ ID NO:1) and Frac3' (CT-CGCTAGCTCACATGGCATAGTCAGGCACGTCATAA-GGATAGCTAGAAGCCATTGTGGCTGCCTGGGTGTC-GGGGAC) (SEQ ID NO:2). The mutant membrane-bound form (mFKN; the mutant form contain mutations that prevent ADAM10/17 from cleaving the FKN into the soluble form, R337A+R338A) was generated by cloning two PCR fragments with primers Frac5'+Fracma (GTAGCCCCACT-GCCTGGGCAGCTGTGGCTGCCTGGGTG) (SEQ ID NO:3) and Frac3' (CTCGCTAGCTCACATGGCATAGT-CAGGCACGTCATAAGGATAGCTAGAAGC CATCACT-GGCACCAGGACGTATGAGTTAC) (SEQ ID NO:4) and Fracms (CACCCAGGCAGCCACAGCTGCCCAGGCA-GTGGGGCTAC) (SEQ ID NO:5).

sFKN and mFKN were cloned into the pTR2-MCS vector at the Age I and Nhe I cloning sites. This vector contains the AAV2 terminal repeats and the hybrid CMV-chicken β-actin promoter for CX3CL1 mRNA transcription. An HA-tag was added to the C-terminus of both sFKN and mFKN with the PCR primers.

Recombinant AAV serotype 9 (rAAV9) vectors were generated and purified as previously described (Carty et al., 2010). rAAV particles are expressed as vector genomes (v/g)/ml. Vector genomes were quantitated using a modified version of the dot plot protocol described by (Zolotukhin et al., 2002). The protocol was modified to use a non-radioactive biotinylated probe for fractalkine generated by PCR. Bound biotinylated probe was detected with IRDye 800CW (Li-Cor Biosciences, Lincoln, Nebr.) and quantitated on the Li-Cor Odyssey. UF11 plasmid was used to generate rAAV9-expressing GFP as previously described (Carty et al., 2008).

In Vitro Cell Culture Experiments sFKN conditioned media was generated by transfection of HEK293 cells with lipofectamine 2000 (Invitrogen) and the pTR2-sFKN plasmid. Cells were incubated in Opti-Mem (Invitrogen; containing 100 U/mL penicillin and 100 ug/mL streptomycin) for 48 hrs. Following incubation, medium was harvested and cleared by centrifugation at 2000×g. The cleared sFKN conditioned medium was used for the proceeding cell culture experiment.

BV2 cells (Blasi et al., 1990) were seeded at $5 \times 10^5$ cells per well in Opti-Mem (Invitrogen; supplemented containing 100 U/mL penicillin and 100 ug/mL streptomycin) of a 24 well plate and allowed to adhere for 16 hrs Immediately prior to treatment, the cells were washed with fresh medium to remove any dead or non-adhered cells. Cells were treated with conditioned media, conditioned media+LPS, LPS, or media alone for 4 hrs. Following incubation, media was removed from each of the four groups and analyzed for TNFα using a commercial ELISA kit (RnD Systems; Minneapolis, Minn.) following the manufacturer's protocol.

Animals

All experiments were conducted in accordance with the National Institute of Health Guide and Use of Laboratory Animals, and were approved by the Institutional Animal Care and Use Committee of the University of South Florida, College of Medicine. CX3CL1$^{-/-}$ mice (Merck Sharp & Dohme Corp.) were backcrossed to the C57BL/6J (WT)

background (Jackson Laboratories; Barharbor, Me.) for greater than 10 generations. Colonies of WT and CX3CL1$^{-/-}$ littermates were maintained at the University of South Florida and genotyping was outsourced using a commercially available service (Transnetyx; Cordova, Tenn.). Twelve to 16 weeks old WT and CX3CL1$^{-/-}$ littermates were used in the proceeding experiments. Mice were pair-housed in environmentally controlled conditions (12:12 h light:dark cycle at 21±1° C.) and provided food and water ad libitum.

Surgical Procedure

Mice for the treatment groups were randomly selected and age stratified to ensure equal representation. Three groups of 12-16 weeks old male CX3CL1$^{-/-}$ mice (n=30 per group) were injected with mFKN, sFKN, or a vector expressing GFP for a viral and protein control, while WT mice were injected with sterile saline (n=60). Briefly, mice from each rAAV group received 1.5 µL at 1×10$^{12}$ vg/mL (2.5 µL/min) bilateral direct injections into the SNpc (AP−2.8, ML±1.4, DV−4.6) using a CED 26-gauge needle (Carty et al., 2010). WT mice and an additional group of CX3CL1$^{-/-}$ mice (n=15) received sterile saline via the same injection parameters.

Acute MPTP Administration

Six weeks following SNpc injections, sFKN, mFKN, and GFP treated CX3CL1−/− mice were weighed and serially injected with MPTP. Additionally, the group of WT mice were weighed and randomly split such that half received either serial injections of MPTP (WT-MPTP) or sterile saline to serve as a double sham for both surgery and injection paradigms (WT-Sham). Lastly, the group of CX3CL1$^{-/-}$ mice that received intracranial saline also received i.p. saline as well (FKN$^{-/-}$ Sham). This group served to examine if there was a genotype effect in the baseline of all endpoints.

MPTP injections were administered as previously described (Cardona et al., 2006). Briefly, MPTP (Sigma Aldrich; 10 mg per kg body weight) was diluted in sterile saline and injected i.p. four times with a one-hour injection interval. Following injections, animal cages were placed on flexible, water heating pads (37° C.) for approximately 24 hours post injection in an effort to maintain body temperature and combat excessive mortality. After 5 days the mice were weighed, any mice that lost greater than 5% body mass were excluded from the study. Mortality ranged from 25-28% and was uniform across all groups of mice exposed to MPTP.

Behavioral Analysis

Five days after MPTP injections, mice were tested for overall balance and motor coordination. This test was performed on an accelerating rotarod apparatus (Ugo Basile, Italy) with a 3 cm diameter rod starting at an initial rotation of 4 RPM accelerating to 40 RPM over 5 minutes. Mice were tested for the time spent on the rod during each of four trials with a 30 min inter-trial interval. Each trial was completed when the mouse fell off the rod (distance of 12 cm) onto a spring-cushioned lever (Rogers et al., 2011).

To assess whether mice have motor coordination deficits and instead of motor learning deficits, only the first three trials (day one) were analyzed. Following behavioral analysis, animals were randomly divided for either perfusions or biochemical analyses.

Immunohistochemistry

Mice were euthanized with pentobarbital (50 mg/kg, i.p.) and were transcardially perfused with phosphate-buffered saline (PBS), followed by 4% paraformaldehyde in PBS. The brains were postfixed in 4% paraformaldehyde for 12 h, after which they were transferred into 30% sucrose in PBS for at least 16 h at 4° C. Exhaustive coronal sections were made at 40 µm using a Microm cryostat (Richard-Allan Scientific, Kalamazoo Mich.) and stored in cryoprotectant at 4° C. Labeling of dopaminergic neurons was performed using an antibody against tyrosine hydroxlase (TH, 1:4000, Immunostar, WI). Neurons were labeled using NeuN (Millipore, 1:500), which is a pan marker for neuronal nuclei.

Activated microglia as well as T cells were visualized with antibodies against CD68, CD11b, and CD3, respectively (Serotec 1:200). Standard staining procedures were conducted on free-floating sections using every sixth section for the entire SNpc and included sections before and after to ensure that the entire structure was sampled. Following incubations (24-48 hrs) with appropriate primary and biotinylated secondary antibodies, sections were treated with Vectastain ABC reagent (Vector labs) and visualized with DAB reaction (Sigma). As a control measure, the specificity of all antibodies was confirmed by omitting primary antibodies.

Stereological Quantification and Imaging

To determine numbers for TH$^+$ and CD$^{3+}$ cells, the optical fractionator method of unbiased stereological cell counting techniques (West et al., 1991) was used with a Nikon Eclipse 600 microscope and quantified using Stereo Investigator software (MicroBrightField, Colchester, Vt.). The virtual grid (150×150 µM) and counting frame (75×75 µM) were optimized to count at least 200 cells per animal with error coefficients less than 0.07. Outlines of the anatomical structures were done using 10×/0.45 objective and cell quantification was conducted using 60×/1.40 objective.

Cell Density Quantification and Imaging

Cell density was measured using a Zeiss Mirax slide scanner, as previously described (Rogers et al., 2011). Briefly, slides with NeuN, CD68, and CD11b immunolabeled sections were scanned and converted into digital image files. Following scanning, the digital images were analyzed for positive area using Zeiss Neuroquant IAE analysis software. An investigator unaware of sample treatment conditions defined the anatomical regions comprising the SNpc for each tissue section. Positive cells were defined using the analysis software based upon their threshold to include both the cell body and processes, while eliminating background values. Data are represented as the average area ratio of positive cells relative to the total measurement area.

Biochemical Analyses Tissue Preparation

Mice used for biochemical studies were euthanatized by rapid decapitation. Brain tissues encompassing the ventral mesencephalon (VM) and striatum were separately dissected and rapidly frozen in liquid nitrogen before storage at −80° C. Tissues were homogenized using an electric tissue homogenizer in 1:10 weight to volume ratio of ice-cold RIPA buffer (Millipore; Billerica Mass.) containing protease inhibitors and EDTA (Pierce; Rockford Ill.). Following homogenization, sample lysates were centrifuged at 10,000×g at 4° C. for 15 minutes, and supernatant was collected. Protein concentration was determined using BCA assay (Pierce). Tissue lysates were used for subsequent Western blot and ELISA analyses.

Western Blot Analysis

50 µg of total protein per lane was loaded onto a 4-15% SDS-polyacrylamide gel (BioRad; Hercules, Calif.) for electrophoresis. Proteins were transferred onto a nitrocellulose membrane for immunodetection. Membranes were subsequently blocked for 1-hour in 5% non-fat dry milk (NFDM) in PBS-tween (PBS-T, 0.1% Tween20). Anti-HA (Roche, 1:500), anti-CX3CL1 (RnD Systems, 1:500), anti-CX3CR1

(Abcam, 1:800), anti-TH (Millipore, 1:500), and mouse beta-actin (Sigma; 1:3000) were incubated overnight at 4° C. in 1% NFDM in PBS-T. Following washes, appropriate secondary antibodies (Li-Cor; Lincoln Nebr.) were incubated for 1-hour at room temperature in 1% NFDM in PBS-T. Membranes were scanned using Li-Cor Odyssey near infrared imager and raw intensity for each band was measured using Li-Cor Odyssey image analysis software. Scanned pseudo-color images were converted to black and white.

ELISA Quantification

CX3CL1, TNFα, and IL-1β concentrations were quantified using standard ELISA technique. VM lysates were run in triplicate at a concentration of 100 µg per well and were incubated overnight at 4° C. Following incubation, the manufacturer's suggested protocol was followed (Raybiotech; Norcross, Ga.). Optical density values for each ELISA plate were measured on a plate reader (BioTek), and sample concentrations were calculated based upon the supplied standard curve. Values were converted from pg/mL to pg/µg of protein loaded.

Data Analysis

All data were analyzed using SPSS software (IBM, v20) and are presented as the mean±standard error of the mean (SEM). Statistical analyses were performed using 3-way ANOVA accounting for genotype, MPTP, and rAAV treatments. Group differences were assessed by Tukey HSD post hoc multiple comparisons test with p values of <0.05 considered significant.

EXAMPLES

Following are examples that illustrate procedures for practicing the invention. These examples should not be construed as limiting. All percentages are by weight and all solvent mixture proportions are by volume unless otherwise noted.

Example 1—Neuroprotective Effects of AAV-Mediated Transfer of Fractalkine

This Example shows that increased FKN expression in the brain region via rAAV-based gene therapy has neuroprotective effects. To examine the therapeutic effects of FKN, FKN is over-expressed using rAAV and cell-specific promoters. Adeno-associated viruses have been used as vectors for gene therapy. rAAV serves as an excellent vector for gene delivery into the CNS. rAAV is non-pathogenic and has low immunogenicity. In addition, all viral genes can be removed from recombinant AAV virus, and long-term expression is attainable.

Three forms of mouse FKN constructs are made and amplified by PCR: 1) the native form (SEQ ID NO:6) (nFKN, which can form both soluble and membrane-bound forms after subsequent processing), 2) the soluble domain of FKN (sFKN) (SEQ ID NO:7), and 3) a protease resistant mutant membrane-bound form (mFKN) (SEQ ID NO:8). To facilitate in vivo detection, hemaggluttinin (HA) tags are attached to the FKN constructs. HEK293 cells are transfected with the FKN plasmid constructs, and Western blot is performed using anti-HA tag antibodies.

Figure 2:
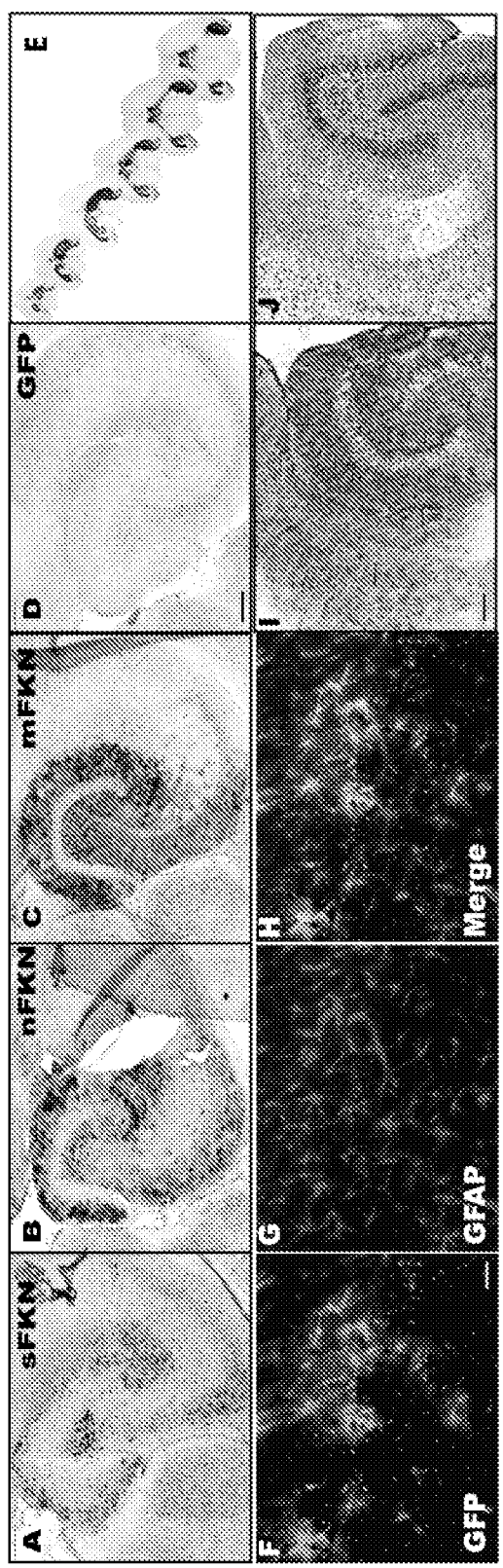
FIG. 2 shows the expression profile of FKN-rAAV recombinant constructs: (A) sFKN; (B) nFKN; (C) mFKN; (D) control anti-HA staining; (E) CED delivery of rAAV9 targets whole HPC; (F) GFAP promoter-GFP; (G) Anti-GFAP; (H) Merge of panels F and G, (I) transduction in HPC with GFAP promoter; (J) transduction in HPC with CBA promoter. A-D, F-H scale 50 μm; I-J scale 200 μm exHPC=hippocampus.
Figure 3:
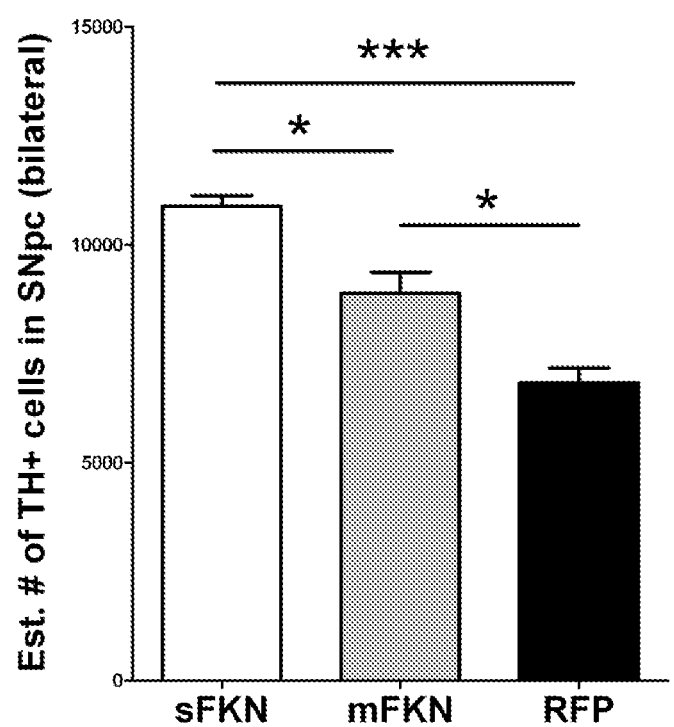
FIG. 3 shows that FKN promotes the survival of TH positive neuron in mice substantia nigra. Mice were treated with rAAV expressing sFKN, mFKN or RFP for 6 weeks prior to MPTP, and were sacrificed 5 days after MPTP exposure.

The Western blot results show that the soluble domain of FKN (sFKN) is secreted into the media, whereas the native form (nFKN) and the mutant form (mFKN) are not detected in the media in a form of soluable bands (FIG. 1a). When the nFKN peptide is processed into a soluble form, the HA tag is cleaved; therefore, no soluble band is detected in the media. FIG. 2A-D shows that the recombinant FKN viral constructs are expressed in vivo in hippocampus. The recombinant FKN viral constructs are also expressed in substantia nigra (SN). FIG. 3 shows that the delivery of FKN into the substantia nigra using rAAV reduces neuron loss in an MPTP-treated mouse model of PD.

In addition, increased expression of either sFKN or mFKN resulted in a significant protection of TH positive neurons, when compared to the control (red fluorescent protein (RFP)). The sFKN offers a slightly higher protection, when compared to mFKN. This can be attributed to several factors, including: 1) the ease of diffusion of the sFKN form, 2) greater increase in sFKN expression, and/or 3) greater effects on microglial activation produced by sFKN.

To obtain astrocyte-specific expression in vitro and in vivo, rAAV vectors under the control of a GFAP promoter are constructed. As shown in FIG. 2F-H, GFP expression is co-localized with the astrocytic protein GFAP, whose expression is detected using an anti-GFAP antibody. FIG. 2I-J shows extensive viral transduction of astrocytes within the brain regions, such as mouse hippocampus. Neuron-specific transduction can also be achieved using CMV-chicken β-actin (CBA) hybrid promoter (Carty et al. (2010)).

The FKN protein can also be delivered into the brain via rAAV using convection-enhanced delivery (CED). Using the CED method, the whole brain structures, such as the hippocampus, can be targeted by the rAAV9 serotype in a single injection (FIG. 2E).

This Example also examines the therapeutic effects of increased FKN expression using an rAAV α-syn animal model, which is shown to produce nigral neuron loss by the present inventors. PD toxin-based models are valuable for understanding dopaminergic cell loss, for testing dopamine replacement therapies, and for identifying interventions to reduce lesion size. However, PD characterized by alpha-synuclein containing Lewy bodies accounts for >90% of sporadic Parkinsonian cases. It has also been proposed that nigral neuronal damage may release aggregated α-syn into the substantia nigra, activating microglia with subsequent production of pro-inflammatory mediators and reactive oxygen species. Compared to toxin-based models of PD, the rAAV α-syn-based animal model can mimic the early stages and slower development of the disease in the substantia nigra. Furthermore, different animal models have shown different responses to therapeutic interventions, e.g. GDNF protects against neuron loss in the toxin based PD model but not in an α-syn model.

Example 2—Transduction of Neuronal Cells Using Recombinant AAV9-FKN Vectors

Both the soluble form and the membrane-bound mutant rAAV9-FKN are produced using a murine version of the CX3CL1 gene driven by the hybrid chicken β-actin cytomegalovirus promoter and are tagged with hemagglutinin (HA) peptide sequence for ease of detection. Prior to virus production, the rAAV vector is tested in HEK293 cells to evaluate sFKN and mFKN proteins are produced from the expression cassette. Cell lysate and conditioned media from transfected cells are examined using Western blot analysis to determine sFKN and mFKN expression. An anti-HA tag Western blot analysis of transfected HEK 293 cells reveals that sFKN is secreted into the media, while mFKN remains only in the cell lysate fraction (FIG. 1a).

The synthetic FKN proteins are biologically active. Briefly, conditioned media from HEK 293 cells transfected with the sFKN plasmid are used to confer bioactivity by measuring the amount of secreted TNF-α from BV2 microglia-like cells. It has been well documented that the induction of cytokine production from microglia as a result of LPS exposure can be blunted if the cells are pretreated with exogenous soluble CX3CL1 peptide (Zujovic et al., 2000; Mizuno et al., 2003; Lyons et al., 2009; Wynne et al., 2010). In accordance with previous literature, the results show that BV2 cells preconditioned with sFKN-conditioned media have an attenuated response to LPS (100 ng/mL) as measured by TNF-α secretion (FIG. 1b). Furthermore, addition of sFKN-conditioned media alone does not induce TNF-α production. This attenuated response is comparable to previous literature (Mizuno et al., 2003; Lyons et al., 2009) given the dilute concentration of CX3CL1 found in sFKN-conditioned media.

The expression of the rAAV9-FKN vectors in vivo is examined Using CX3CL1 null mice, each vector is bilaterally injected into the mouse SNpc. Six weeks post injection, harvested brain tissues are analyzed for sFKN and mFKN expression by Western blot. Using an anti-mouse CX3CL1 antibody, sFKN and the mFKN proteins, having a molecular weight consistent with the literatures (Bachstetter et al., 2009), are produced by in vivo expressions of the rAAV-FKN construct encoding the sFKN and the mFKN. Importantly, mFKN shows only a single band, indicating that the dibasic arginine mutation effectively inhibits cleavage by ADAM10/17 (FIG. 1c). Furthermore, direct injection using CED method (Carty et al., 2010) with rAAV variants results in transduction of various neurons throughout the SNpc (FIG. 1d). Viral transduction is not limited to neurons of the SNpc, as other non-dopaminergic neurons are transduced. Of these populations, rAAV vectors result in effective transduction of a variety of neurons (with 90% or higher transduction rate). Additionally, parenchymal injections via CED results in neuronal transduction with minimal astrocytic expression.

Figure 7:
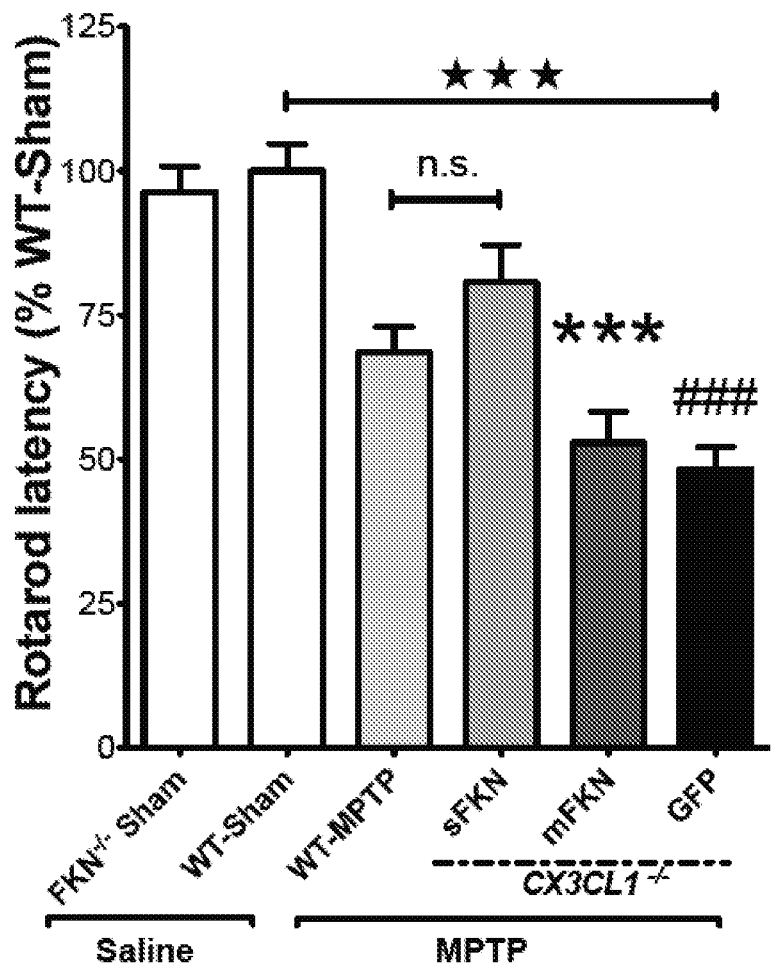
FIG. 7 shows that sFKN reduces impairment of motor coordination in mice caused by 1-methyl-4-phenyl-1,2,3,6-tetrahydropyridine (MPTP) injections. Five days after the last injections of MPTP or saline, mice are subjected to behavioral analysis to analyze balance and coordination on an accelerating rotarod. Motor coordination is assessed by the average of three trials during raining. FKN$^{-/-}$ sham group and the WT-sham group exhibit similar level of motor coordination. Exposure to MPTP induces significant deficits in motor coordination, when compared to WT-Sham mice that receives sterile saline (3-way ANOVA; $F(1,145)=42.11$, ★★★p<0.001). CX3CL1$^{-/-}$ mice treated with sFKN have significantly better motor coordination than that of mice treated with mFKN (Tukey HSD; ***p=0.002) or GFP (Tukey HSD; ### p<0.001). Additionally, treatment with sFKN reduces the level of motor coordination deficits observed in MPTP-exposed mice, and the sFKN-treated mice have motor coordination ability similar to that of the WT-sham mice (Tukey HSD; p=0.380). Data are presented as mean time in seconds as a percentage of WT-Sham±SEM. n.s.=not significant.

Example 3—Treatment of MPTP-Induced Impairment of Motor Coordination by the Soluble Isoform of FKN The effects of rAAV-sFKN and rAAV-mFKN on MPTP-induced motor deficits are examined using an accelerating rotarod. FKN$^{-/-}$ Sham mice display no motor coordination impairment when compared to WT-Sham (FIG. 7). Five days after the last MPTP injection, all MPTP-treated groups display a significant trend for performance impairment (F (1, 145)=42.11, p<0.001), as measured by average latency to fall across three trials compared to WT-Sham mice (FIG. 7). Treatment with sFKN significantly improves MPTP-induced behavioral deficits when compared to mFKN (p=0.002) and GFP (p<0.001) viral control.

Figure 8:
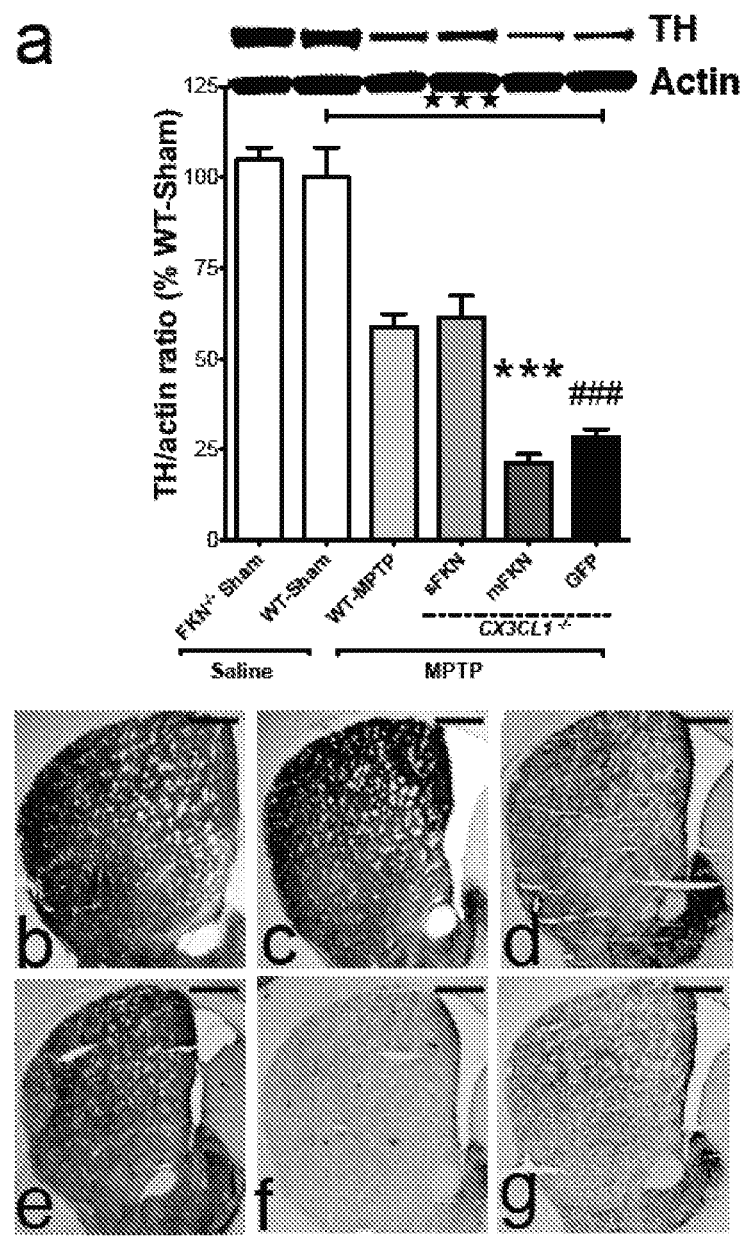
FIG. 8 shows that sFKN reverses or reduces the depletion of tyrosine hydroxylase (TR) in the striatum due to MPTP treatment Both hemispheres are dissected seven days following the last MPTP or saline injections for biochemical analysis. (A) Western blot analysis reveals that MPTP exposure significantly reduces the availability of TH in the striatum (3-way ANOVA; $F(1, 23)=34.42$, ★★★p<0.001). FKN$^{-/-}$ sham animals have no distinguishable difference in TH production when compared to WT-Sham mice. CX3CL1$^{-/-}$ mice expressing sFKN in the SNpc have an attenuated loss of TH compared to mFKN (Tukey HSD; ***p<0.001) and GFP (Tukey HSD; ### p<0.001) expressing mice. There are no significant differences between CX3CL1$^{-/-}$ mice expressing either mFKN or GFP (Tukey HSD; p=0.627). (B-G) Representative immunostaining in the striatum shows progressive loss of TH for (B) FKN$^{-/-}$ sham (C) WT-Sham, (D) WT-MPTP, (E) sFKN, (F) mFKN, and (G) GFP groups. Data are presented as the mean band density ratio (n=5 per group) of TH to actin as a percentage WT-Sham±SEM. Scale bars are 200 μm.

Following rotarod performance assessment, mice are sacrificed and striatal tissues are dissected for biochemical analysis. Consistent with each group's rotarod performance, Western blot analysis reveals a significant loss of striatal tyrosine hydroxylase (TH) as a result of MPTP administration (p<0.001), ranging from 40-75% (FIG. 8a). sFKN treatment attenuates exhaustive striatal TH loss by 30-35% when compared to mFKN (p<0.001) or GFP groups (p<0.001), respectively.

Example 4—Treatment of MPTP-Induced Neurodegeneration of SNPC by the Soluble Isoform of FKN Disruption of CX3CL1 signaling via genetic ablation of CX3CR1 in mice exacerbates MPTP neurotoxicity in SNpc (Cardona et al., 2006). Seven days after the last MPTP injection, mice are transcardially perfused with a buffered paraformaldehyde solution and brain tissues are removed. The level of MPTP induced neurodegeneration in the SNpc is determined by stereological quantification of TH (FIG. 9a) and by measuring the density of NeuN (FIG. 9b) staining.

Figure 9:
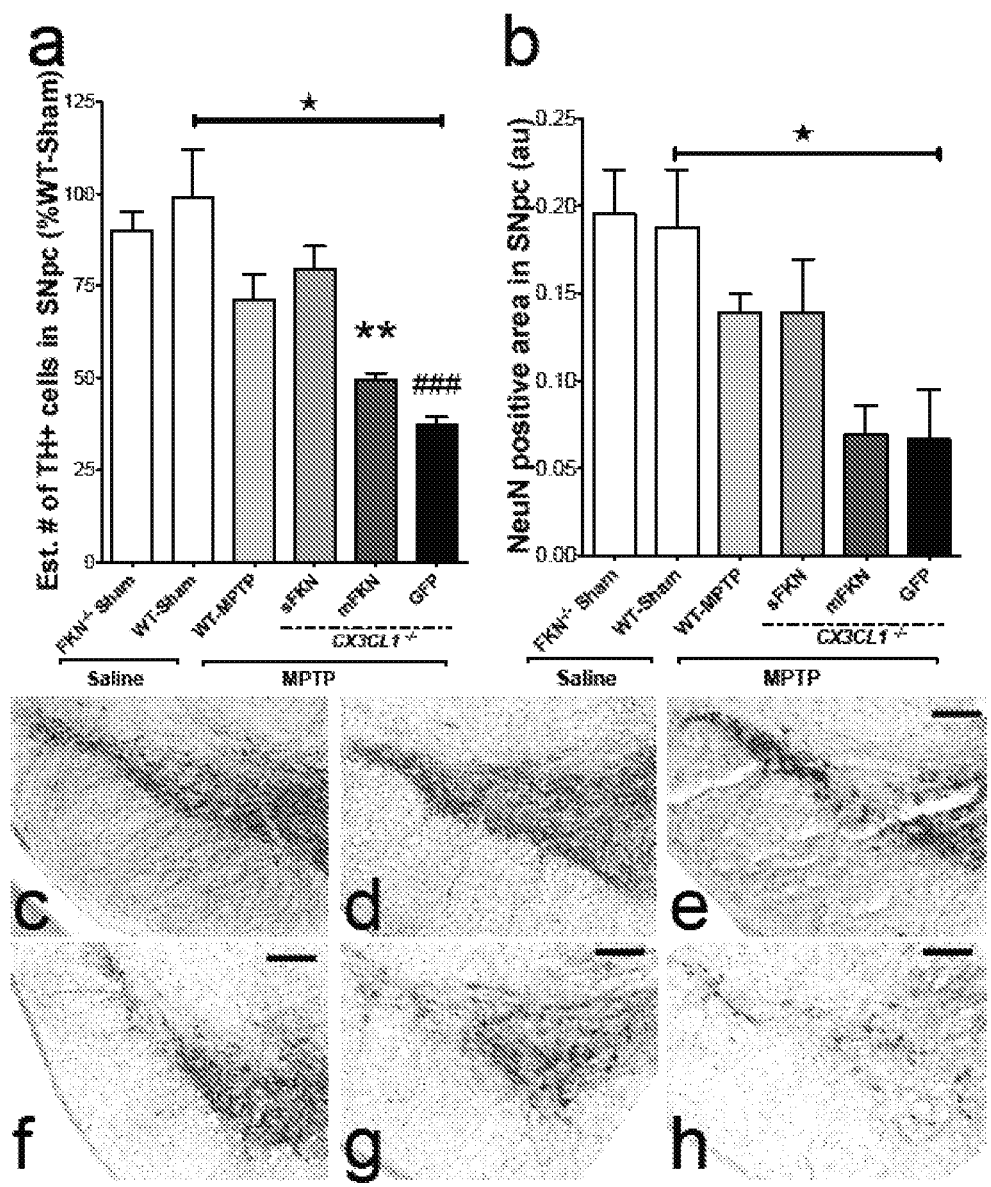
FIG. 9 shows stereological analysis of TH-positive neurons in the SNpc. TH immunoreactivity is analyzed in the SNpc of coronal sections of mice seven days after the final MPTP or saline injections. (A) Exposure to MPTP results in a marked reduction in the estimated number of TH-positive cells in the SNpc (3-way ANOVA; $F(1, 1)=4.733$, ★p=0.050) when compared to WT-Sham. FKN$^{-/-}$ sham animals exhibit no phenotypical differences in TH+ cell counts when compared to WT-Sham mice. sFKN treatment results in the most significant TH-neuroprotection when compared to mFKN (Tukey HSD; **p=0.003) and GFP (Tukey HSD; ### p<0.001) treatments. There is no significant difference in the level of TH+ cells between CX3CL1$^{-/-}$ mice expressing either mFKN or GFP (p=0.324). (B) Graph of NeuN$^+$ cell density in the SNpc. Although injections with MPTP reduce the immunoreactivity of NeuN+ cells compared to WT-Sham (3-way ANOVA; $F(1, 18)=6.81$, ★p=0.018), there are no significant differences among group interactions (2-way ANOVA; $F(3, 12)=3.14$, p=0.065). Akin to TH+ cell counts, there are no differences between FKN$^{-/-}$ sham and WT-Sham animals for NeuN density. The mFKN- and GFP-treated CX3CL1$^{-/-}$ mice show a lower level of NeuN immunoreactivity. (C-H) Representative immunostaining for TH$^+$ cells in the SNpc for (C) FKN$^{-/-}$ sham (D) WT-Sham, (E) WT-MPTP, (F) sFKN, (G) mFKN, and (H) GFP treated groups. Data are presented as mean estimate of TH+ cells or mean density ratio as a percentage of WT-Sham±SEM. Scale bars are 200 μm.

FKN$^{-/-}$ Sham mice show no significant reduction in the number of TH positive or the density of NeuN stained neurons, when compared to WT-Sham; the results indicate that genetic disruption of CX3CL1 signaling, alone, does not produce a PD like phenotype (FIG. 9a,b).

Compared to WT-Sham, MPTP exposure produces a marked reduction in the estimated number of TH positive cells across all groups (F (1, 12)=4.733, p=0.050). As previously shown by Cardona et al. (2006), MPTP produced a larger lesion in the CX3CL1$^{-/-}$ mice.

sFKN treatment attenuates MPTP-induced dopaminergic cell loss, when compared to mFKN (p=0.003) and GFP (p<0.001) treatment. In addition, exposure to MPTP reduces the NeuN positive cell density in the SNpc (F (1, 12)=4.733, p=0.050). Consistent with the results with respect to the TH+ cell estimates, treatment with sFKN, but not mFKN, results in increased density of NeuN-labeled neurons in the SNpc, although there is no significant differences when groups are compared amongst each other (F(1,12)=3.14, p=0.065).

Example 5—Administration of MPTP does not Alter CX3CL1-CX3CR1 Signaling

Figure 10:
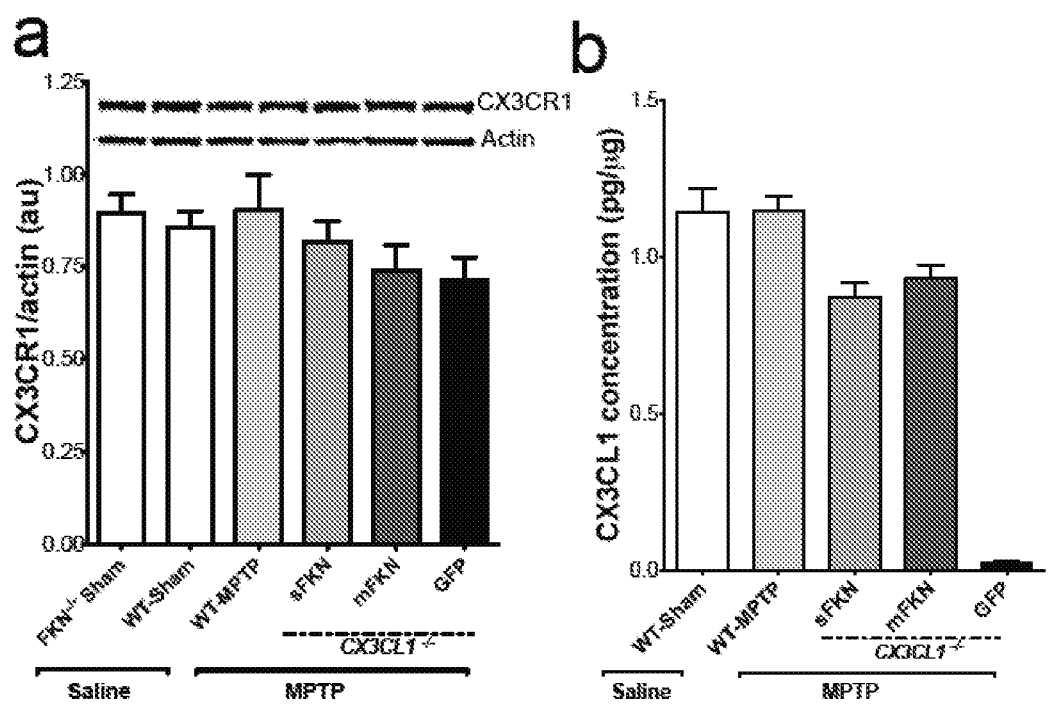
FIG. 10 shows that MPTP does not alter CX3CL1-CX3CR1 signaling in the VM. Tissue lysates from the VM of each group are analyzed for protein levels of either CX3CR1 by Western blot and CX3CL1 by ELISA. (A) Representative bands for CX3CR1 and Actin for each group from Western blot analysis of VM tissue lysates using an anti-mouse CX3CR1 antibody. There are no significant alterations of CX3CR1 protein levels as a result of either MPTP or saline injections. In addition, neither the presence nor absence of CX3CL1 (regardless of isoform) affects protein levels of CX3CR1 (3-way ANOVA; $F(1, 19)=0.66$, p=0.428) (B) VM lysates are analyzed for CX3CL1 concentrations by standard ELISA. Exposure to MPTP does not alter the production of CX3CL1 compared to WT-Sham (3-way ANOVA; $F(1, 23)=3.74$, p=0.066). In addition, each rAAV-FKN vector sufficiently restores the levels of CX3CL1 in the VM to that resembling WT-Sham. Importantly, the rAAV-sFKN and rAAV-mFKN vectors result in a similar level of CX3CL1 expression (sFKN vs. mFKN; Tukey HSD; p=0.703). Data are presented as the mean band density ratio of CX3CR1 to Actin and the mean concentration of CX3CL1 in μg/μg±SEM. au arbitrary units.

Recent literatures have suggested that acute inflammatory insults can down-regulate both transcript and protein levels of CX3CR1 on microglia (Kremlev and Palmer, 2005; Wynne et al., 2010). Western blot analysis is performed to determine CX3CR1 expression in VM tissue lysates (FIG. 10a). Acute exposure to MPTP does not affect (F (1, 19)= 0.66, p=0.428) the protein levels of CX3CR1 in vivo. Additionally, neither the administration of rAAV-FKN (rAAV-sFKN or rAAV-mFKN) vectors nor the complete absence of CX3CL1 in the GFP group alters CX3CR1 protein levels in the VM (F (3, 13)=1.47, p=0.268).

The results show that expression of CX3CR1 is constitutive (Harrison et al., 1998), and does not depend on the type of CX3CL1 isoform or its concentration in the surrounding milieu. Additionally, the production of CX3CL1 from the rAAV-sFKN vector and the rAAV-mFKN vector in the VM is quantified. Each rAAV-FKN vector can restore CX3CL1 levels resembling that of WT-Sham, and the rAAV-sFKN vector and the rAAV-mFKN vector produces similar concentrations of CX3CL1 (FIG. 10b). The results also show that MPTP exposure does not affect the production of CX3CL1 (WT-Sham vs. WT-MPTP; p>0.05).

Example 6—Induction of CD68 and CD11B Reactive Microglia is Attenuated by the Soluble Isoform of FKN Microglial activation has been implicated in the propagation of SNpc neurotoxicity in several animal models of PD. An intact CX3CL1 to CX3CR1 signaling axis dampens the neurotoxic effects of both 6-OHDA and MPTP. Post-mortem analysis of idiopathic PD patients has revealed strong immunoreactivity for CD68, a marker of phagocytic microglia (Croisier et al., 2005; Vroon et al., 2007). In addition, administration of MPTP has been reliably shown to induce this phagocytic microglia phenotype in the SNpc of mice (Vroon et al., 2007; Chung et al., 2010; Chung et al., 2011).

Figure 11:
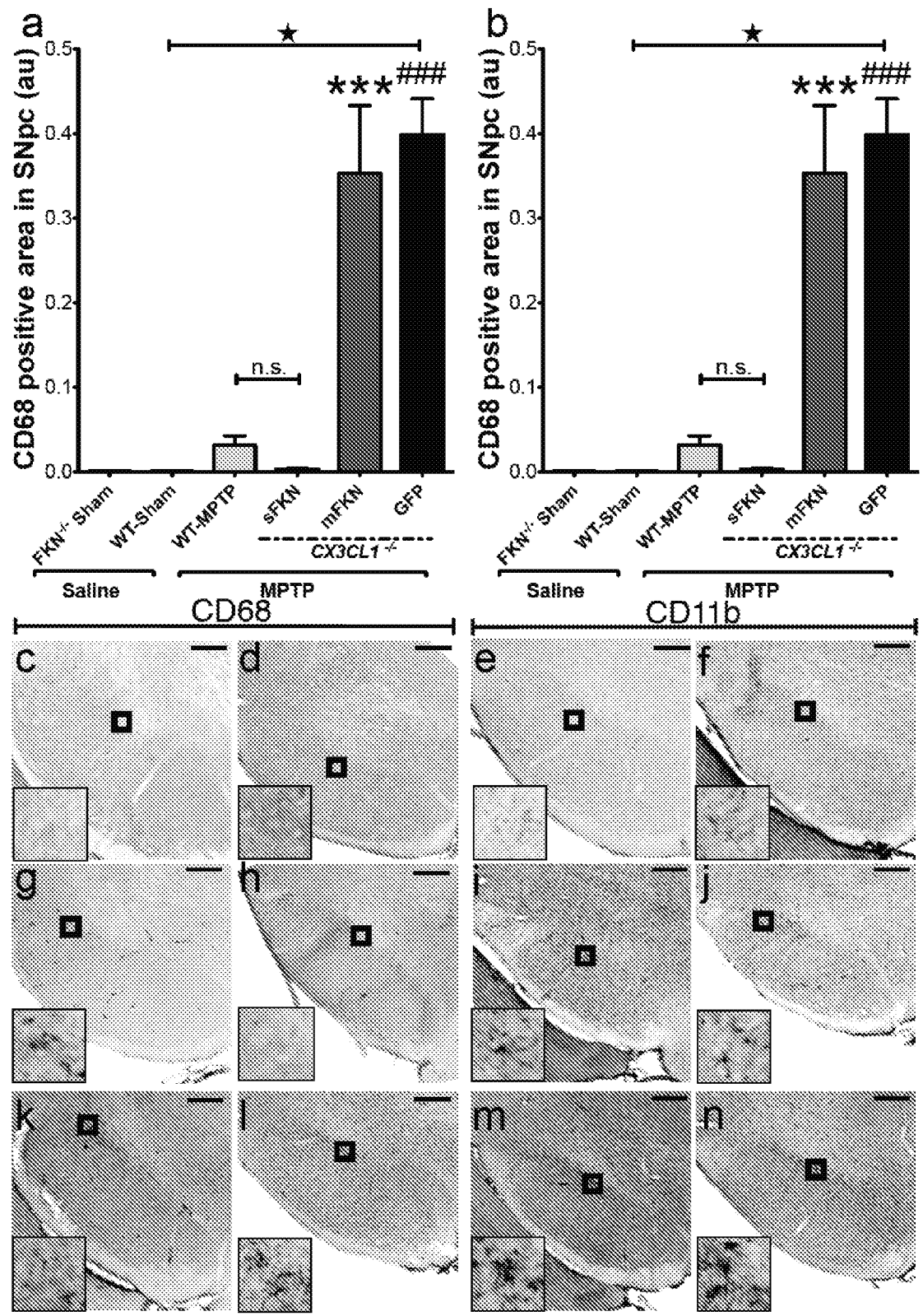
FIG. 11 shows that the activation of microglia in the SNpc induced by MPTP is ameliorated by sFKN. Two markers of microglia activation in the SNpc are quantified using densitometric analysis. (A) MPTP exposure results in a significant immunoreactive profile for CD68, when compared to saline injections (3-way ANOVA; $F(1,26)$ 4.25, ★p=0.046). No difference is observed in CD68 staining for FKN$^{-/-}$ sham mice, when compared to WT-Sham. CD68 immunoreactivity is noticeably absent in sFKN treated mice, akin to levels found in WT-Sham. The sFKN expressing mice also exhibit a dramatic reduction in CD68 immunoreactivity relative to CX3CL1$^{-/-}$ mice expressing either mFKN (Tukey HSD; *p<0.001) or GFP (Tukey HSD; ### p<0.001). Although an induction of the CD68 phenotype is observed in WT-MPTP mice, no significant induction of CD68 in sFKN mice (Tukey HSD; p=0.971). (B) Densitometric analysis of CD11b immunoreactivity in the SNpc. MPTP exposure induces significant upregulation of CD11b immunoreactivity when compared to saline injections (3-way ANOVA; $F(1, 27)$=7.35, ★p=0.021). There is a slight increase in CD11b reactivity for FKN$^{-/-}$ sham mice, but this is not significant compared to WT-Sham group. CX3CL1$^{-/-}$ mice expressing sFKN in the SNpc have a blunted response to MPTP compared to mFKN (Tukey HSD; *p=0.007) and GFP (Tukey HSD; ### p<0.001) expressing mice. Similar to CD68 immunoreactivity, there are no significant differences between WT-MPTP and CX3CL1$^{-/-}$ mice expressing sFKN (Tukey HSD; p=0.792). (C-N) Representative immunoreactivity of CD68 and CD11b reactive microglia in the SNpc for (C,E) FKN$^{-/-}$ sham (D,F) WT-Sham, (G,I) WT-MPTP, (H,J) sFKN, (K,M) mFKN, and (L,N) GFP groups, respectively. Inset images are high-power magnifications of their respective staining taken from the approximate location of the small black box. Data are presented as the mean area ratio±SEM. Scale bars are 200 μm. au=arbitrary units. n.s=not significant.

Quantification of CD68 positive cell density reveals a significant induction of microglia reactivity (FIG. 11a) as a result of MPTP injections, when compared to WT-Sham (F(1, 26)=4.25, p=0.046). In addition, loss of CX3CL1 (FKN$^{-/-}$ Sham) is not sufficient to induce significant upregulation of CD68 immunoreactivity. CD68 immunoreactivity is most profound in both the mFKN (p=0.001) and GFP (p<0.001) treated groups, when compared to sFKN-treated groups. Furthermore, sFKN treated mice resembled that of WT-MPTP (p=0.971) in that there are very few CD68 positive cells. The results show that mice treated with mFKN have a CD68 phenotype similar to that of mice treated with control AAV-GFP vector (FIG. 7k,l p=0.913).

Figure 12:
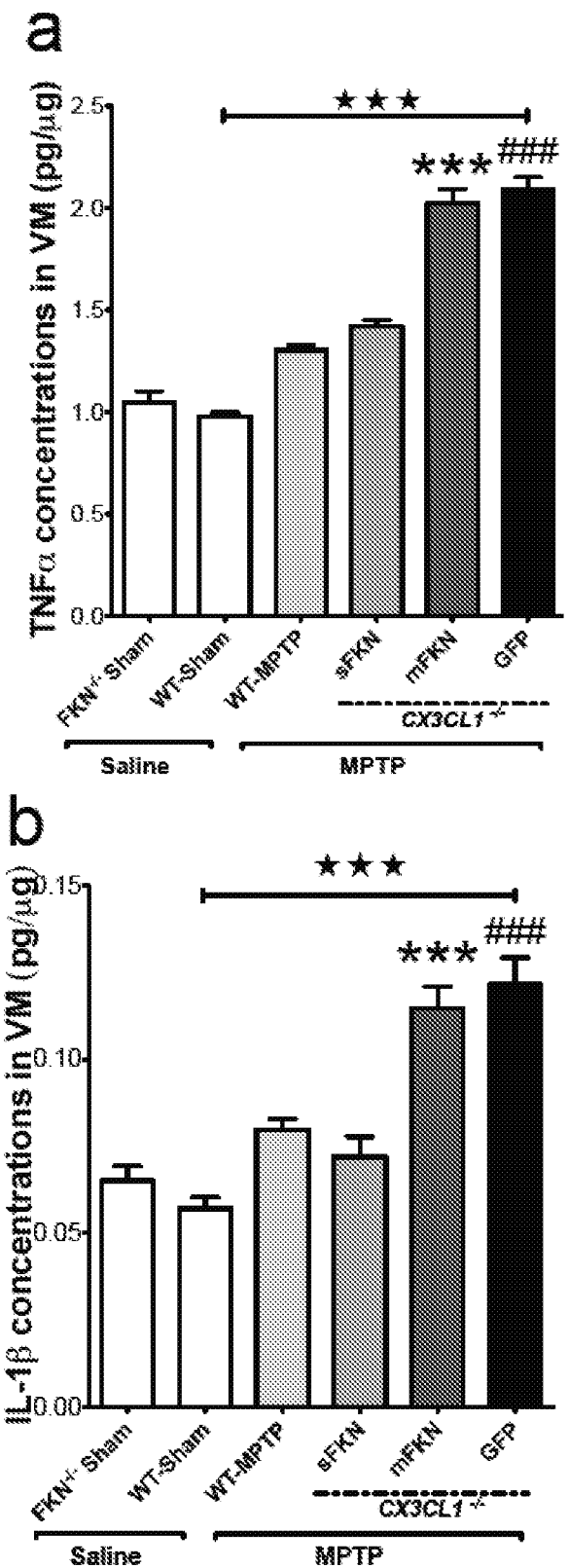
FIG. 12 shows that induction of pro-inflammatory cytokines is attenuated in CX3CL1$^{-/-}$ mice expressing sFKN. TNFα and IL-1β concentrations are measured using standard ELISA techniques for VM lysates. (A) TNFα concentrations are upregulated following MPTP administration (3-way ANOVA; $F(1, 23)$=18.36, ★★★p<0.001). Comparatively, CX3CL1$^{-/-}$ mice expressing sFKN in the SNpc have significantly lower concentrations of TNFα relative to mFKN (Tukey HSD; *p<0.001) and GFP (Tukey HSD; ### p<0.001) expressing mice. There are no significant differences between sFKN and WT-MPTP (Tukey HSD; p=0.384) or mFKN and GFP (Tukey HSD; p=0.773). (B) The IL-1β concentrations in the VM are significantly upregulated for mice exposed to MPTP (3-way ANOVA; $F(1,23)$=11.97, ★★★p=0.002). Similar to the pattern of TNFα, IL-1β concentrations in CX3CL1$^{-/-}$ mice expressing sFKN are significantly blunted compared to both mFKN (Tukey HSD; *p=0.001) and GFP (Tukey HSD; ### p<0.001). As observed with TNFα, there are no significant differences in IL-1β concentrations between WT-MPTP and sFKN (Tukey HSD; p=0.785) or mFKN and GFP (Tukey HSD; p=0.845) expressing mice. Data are presented as the mean±SEM.
Figure 13:
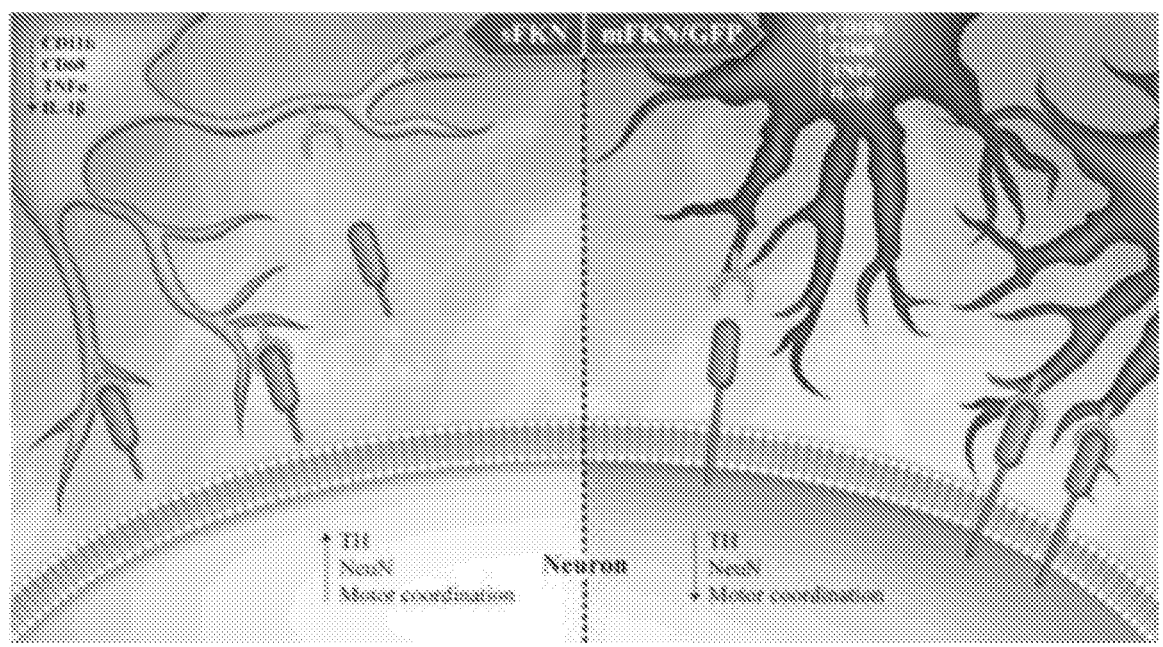
FIG. 13 shows that the soluble isoform of CX3CL1, not the membrane-bound form, is neuroprotective in an MPTP model of PD. It is postulated that neuron to microglia interaction is either through a soluble isoform (sFKN) or through a membrane-anchored isoform (mFKN). It is feasible that mFKN allows direct neuron-microglia interaction. In accordance with the present invention, the data indicate that the sFKN isoform provides neuroprotection through blunting the neurotoxic/pro-inflammatory response following MPTP exposure. Mice expressing sFKN have an ameliorated response to MPTP exposure when compared to mice expressing only mFKN in the SNpc. Mice expressing mFKN phenotypically resemble mice lacking CX3CL1 (GFP) in response to MPTP exposure. The results do not show that expressing mFKN, alone, induces neuroinflammation in the MPTP model of PD.

A broader marker for microglia activation is analyzed using an antibody for CD11b. Immunolabeled CD11b microglia have previously been shown to increase reactivity following administration of the dopaminergic neurotoxin MPTP in the SNpc (Wu et al., 2003; Chung et al., 2011). Mice exposed to MPTP had a significant increase in CD11b reactive microglia (FIG. 12b), when compared to WT-Sham (F(1, 27)=7.35, p=0.021). FKN$^{-/-}$ Sham mice display no induction phenotype for CD11b, when compared to WT-Sham mice. Mice received sFKN injections again presented a similar CD11b expression phenotype as WT-MPTP (p=0.792). A strong induction of CD11b density by MPTP exposure is observed in the SNpc of both mFKN (FIG. 11m, p=0.007) and GFP (FIG. 11n, p<0.001) treated groups, when compared to sFKN (FIG. 11j) treated CX3CL1 null mice. Additionally, following MPTP exposure, similar levels of CD11b immunoreactivity are observed between mFKN and GFP treated CX3CL1 null mice (p=0.499).

Recent literature has identified a subset of cytotoxic (CD4$^+$CD28$^-$) T cells express CX3CR1, which is thought to mediate T cell entry to brain parenchyma in an animal model of multiple sclerosis (Broux et al., 2011). The results show an increase in CD3$^+$ cells in the SNpc following MPTP exposure, whereas no difference in the level of CD3$^+$ cells is observed sFKN and mFKN treated mice.

Example 7—The Soluble Isoform of FKN Reduces the Induction of Pro-Inflammatory Cytokines by MPTP Post-mortem analysis of human PD tissue shows that microglia are immunoreactive for multiple pro-inflammatory cytokines, including TNFα and IL-1β (McGeer and McGeer, 2004). In addition, mice that are genetically altered to inhibit cytokine production or are deficient in receptors for these cytokines provide neuroprotection in the SNpc following MPTP exposure (Klevenyi et al., 1999; Sriram et al., 2002).

As CX3CL1 signaling has been shown to attenuate the production of these cytokines in vitro and in vivo following inflammatory stimuli, the Example evaluates the anti-inflammatory properties of each rAAV-sFKN and rAAV-mFKN treatment in response to MPTP exposure in the CX3CL1 null mice. Tissue lysate of the VM are analyzed using standard ELISA techniques for the pro-inflammatory cytokines TNFα and IL-1β. The results show that there is no significant change in these cytokines for FKN$^{-/-}$ Sham mice, when compared to WT-Sham. MPTP treatment significantly unregulates the production of TNF-α (FIG. 12a; F(1, 23)=18.36, p<0.001) and IL-1β (FIG. 12b; F(1, 23)=11.97, p=0.002), when compared to all treatment groups. The results show an increase in activated microglia (CD11b$^+$ and CD68$^+$) following exposure to MPTP. sFKN attenuated the production of both TNF-α (p<0.001) and IL-1β (p<0.001), when compared to mFKN and GFP treated mice. The production levels of TNF-α (p<0.001) and IL-1β in sFKN mice are similar to that of the WT-MPTP group.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Bachstetter A D, Morganti J M, Jerriberg J, Schlunk A, Mitchell S H, Brewster K W, Hudson C E, Cole M J, Harrison J K, Bickford P C, Gemma C (2009) Fractalkine and CX(3)CR1 regulate hippocampal neurogenesis in adult and aged rats. Neurobiology of aging.

Bezard E, Przedborski S (2011) A tale on animal models of Parkinson's Disease. Movement disorders: official journal of the Movement Disorder Society 26:993-1002.

Bhaskar K, Konerth M, Kokiko-Cochran O N, Cardona A, Ransohoff R M, Lamb B T (2010) Regulation of Tau Pathology by the Microglial Fractalkine Receptor. Neuron 68:19-31.

Biber K, Neumann H, Inoue K, Boddeke H W G M (2007) Neuronal 'On' and 'Off' signals control microglia. Trends Neurosci 30:596-602.

Blasi E, Barluzzi R, Bocchini V, Mazzolla R, Bistoni F (1990) Immortalization of murine microglial cells by a v-raf/v-myc carrying retrovirus. Journal of Neuroimmunology 27:229-237.

Borroni E M, Mantovani A, Locati M, Bonecchi R (2010) Chemokine receptors intracellular trafficking. Pharmacology & therapeutics 127:1-8.

Brochard V, Cotnbadière B, Prigent A, Laouar Y, Perrin A, Beray-Berthat V. Bonduelle O, Alvarez-Fischer D, Callebert J, Launay J-M, Duyckaerts C, Flavell R A, Hirsch E C, Hunot S (2008) Infiltration of CD4+ lymphocytes into the brain contributes to neurodegeneration in a mouse model of Parkinson disease. The Journal of clinical investigation.

Broux B, Pannemans K, Zhang X, Markovic-Plese S, Brockmans T, Eijnde B O, Van Wijmeersch B, Somers V, Geusens P, van der Pol S, van Horssen J, Stinissen P, Hellings N (2011) CX(3)CR1, drives cytotoxic CD4(+) CD28(−) T cells into the brain of multiple sclerosis patients. Journal of autoimmunity.

Cardona A E, Sasse M E, Liu L, Cardona S M, Mizutani M, Savarin C, Hu T, Ransohoff R M (2008) Scavenging roles of chemokine receptors; chemokine receptor deficiency is associated with increased levels of ligand in circulation and tissues. Blood 112:256-263.

Cardona A E, Pioro E P, Sasse M E, Kostenko V, Cardona S M, Dijkstra I M, Huang D, Kidd G, Dombrowski S, Dutta R, Lee J-C, Cook D N, Jung S, Lira S A, Littman D R, Ransohoff R M (2006) Control of microglial neurotoxicity by the fractalkine receptor. Nat Neurosci 9:917-924.

Carty N, Lee D, Dickey C, Ceballos-Diaz C, Jansen-West K, Golde T E, Gordon M N, Morgan D, Nash K (2010) Convection-enhanced delivery and systemic mannitol increase gene product distribution of AAV vectors 5, 8, and 9 and increase gene product in the adult mouse brain. Journal of neuroscience methods 194:144-153.

Carty N C, Nash K, Lee D, Mercer M, Gottschall P E, Meyers C, Muzyczka N, Gordon M N, Morgan D (2008) Adeno-associated viral (AAV) serotype 5 vector mediated gene delivery of endothelin-converting enzyme reduces Abeta deposits in APP+PSI transgenic mice. Mol Ther 16:1580-1586.

Chapman G A, Moores K, Harrison D, Campbell C A, Stewart B R, Strijbos P J (2000) Fractalkine cleavage from neuronal membranes represents an acute event in the inflammatory response to excitotoxic brain damage. J Neurosci 20:RC87.

Chung Y C, Kim S R, Jin B K (2010) Paroxetine Prevents Loss of Nigrostriatal Dopaminergic Neurons by Inhibiting Brain Inflammation and Oxidative Stress in an Experimental Model of Parkinson's Disease. The Journal of immunology 185:1230-1237.

Chung Y C, Kim S R, Park J-Y, Chung E S, Park K W, Won S Y, Bok E, Jin M, Park E S, Yoon S-H, Ko H W, Kim Y S, Jin B K (2011) Fluoxetine prevents MPTP-induced loss of dopaminergic neurons by inhibiting microglial activation. Neuropharmacology 60:963-974.

Croisier E, Moran L B, Dexter D T, Pearce R K B, Graeber M B (2005) Microglial inflammation in the parkinsonian substantia nigra: relationship to alpha-synuclein deposition. Journal of Neuroinflammation 2:14.

Euhrmann M, Bittner T, Jung C K E, Burgold S, Page R M, Mitteregger G, Haass C, Laferla F M, Kretzschmar H, Herms J (2010) Microglial Cx3cr1 knockout prevents neuron loss in a mouse model of Alzheimer's disease. Nature neuroscience 13:411-413.

Garcia G E, Xia Y, Chen S, Wang Y, Ye R D, Harrison J K, Bacon K B, Zenves H G, Feng L (2000) NF-kappaB-dependent fractalkine induction in rat aortic endothelial cells stimulated by IL-1beta, TNF-alpha, and LPS. J Leukoc Biol 67:577-584.

Garton K J, Gough P J, Blobel C P, Murphy G, Greaves D R, Dempsey P J, Raines E W (2001) Tumor necrosis factor-alpha-converting enzyme (ADAM17) mediates the cleavage and shedding of fractalkine (CX3CL1), Biol Chem 276:37993-38001.

Harrison 1K, Jiang Y, Chen 5, Xia Y, Maciejewski D, McNamara R K, Streit A A/J, Salafranca M N, Adhikari S, Thompson D A, Both P, Bacon K B, Feng L (1998) Role for neuronally derived fractalkine in mediating interactions between neurons and CX3CR1-expressing microglia. Proc Natl Acad Sci LISA 95:10896-10901.

Hundhausen C, Schulte A, Schulz B, Andrzejewski M G, Schwarz N, von Hundelshausen P, Winter U, Paliga K. Reiss K, Saftig P, Weber C, Ludwig A (2007) Regulated shedding of transmembrane chemokines by the disintegrin and metalloproteinase 10 facilitates detachment of adherent leukocytes. J Immunol 178:8064-8072.

Jackson-Lewis V, Jakowec M, Burke R E, Przedborski S (1995) Time course and morphology of dopaminergic neuronal death caused by the neurotoxin 1-methyl-4-phenyl-1,2,3,6-tetrahydropyridine. Neurodegeneration: a journal for neurodegenerative disorders, neuroprotection, and neuroregeneration 4:257-269.

Kim K-W, Vallon-Eberhard A, Zigmond E, Earache J, Shezen E, Shakhar G, Ludwig A, Lira S A, Jung S (2011) In vivo structure/function and expression analysis of the CX3C chemokine fractalkine, Blood 118:e156-167.

Kim Y S, Joh T H (2006) Microglia, major player in the brain inflammation: their roles in the pathogenesis of Parkinson's disease. Experimental; molecular medicine 38:333-347.

Klevenyi P, Andreassen O, Ferrante R J, Schleicher J R, Friedlander R M, Beal M E (1999) Transgenic mice expressing a dominant negative mutant interleukin-1beta converting enzyme show resistance to MPTP neurotoxicity. Neuroreport 10:635-638.

Kremlev S G, Palmer C (2005) Interleukin-10 inhibits endotoxin-induced pro-inflammatory cytokines in microglial cell cultures. Journal of Neuroimmunology 162:71-80.

Lee S, Varvel N H, Konerth M E, Xu G, Cardona A E, Ransohoff R M, Lamb B T (2010) CX3CR1Deficiency Alters Microglial Activation and Reduces Beta-Amyloid Deposition in Two Alzheimer's Disease Mouse Models. The American journal of pathology.

Ludwig A, Weber C (2007) Transmembrane chemokines: versatile 'special agents' in vascular inflammation. Thromb Haemost 97:694-703.

Lyons A, Lynch A M, Downer E J, Hanley R, O'Sullivan J B, Smith A, Lynch M A (2009) Fractalkine-induced activation of the phosphatidylinositol-3 kinase pathway attenuates microglial activation in vivo and in vitro, Journal of Neurochemistry 110:1547-1556.

Maciejewski-Lenoir D, Chen S, Feng L, Maki R, Bacon K B (1999) Characterization of fractalkine in rat brain cells: migratory and activation signals for CX3CR-1-expressing microglia. Journal of immunology (Baltimore, Md.: 1950) 163:1628-1635.

McGeer P L, McGeer E G (2004) Inflammation and neurodegeneration in Parkinson's disease. Parkinsonism & Related Disorders 10:S3-S7.

Mizuno T, Kawanokuchi J, Numata K, Suzumura A (2003) Production and neuroprotective functions of fractalkine in the central nervous system. Brain Res 979:65-70.

Mizutani N, Sakurai T, Shibata T, Uchida K, Fujita J, Kawashima R, Kawamura Y I, Toyama-Sorimachi N, Imai T, Dohi T (2007) Dose-dependent differential regulation of cytokine secretion from macrophages by fractalkine. J Immunol 179:7478-7487.

Neel N F, Schutyser E, Sai J, Fan G-H, Richmond A (2005) Chemokine receptor internalization and intracellular trafficking. Cytokine & growth factor reviews 16:637-658.

Pabon M M, Bachstetter A D, Hudson C E, Gemma C, Bickford P C (2011) CY3CL1 reduces neurotoxicity and microglial activation in a rat model of Parkinson's disease. Journal of Neuroinflammation Przedborski S, Jackson-Lewis V, Naini A B, Jakowec M, Petzinger G, Miller R, Akram M (2001) The parkinsonian toxin 1-methyl-4-phenyl-1,2,3,6-tetrahydropyridine (MPTP): a technical review of its utility and safety. Journal of Neurochemistry 76:1265-1274.

Ransohoff R M, Liu L, Cardona A E (2007) Chemokines and chemokine receptors: multipurpose players in neuroinflammation Int Rev Neurobiol 82:187-204.

Ré D B, Przedborski S (2006) Fractalkine: moving from chemotaxis to neuroprotection. Nat Neurosci 9:859-861.

Rogers J T, Morganti J M M, Bachstetter A D, Hudson C E, Peters M M, Grimmig B A, Weeber E J, Bickford P C, Gemma C (2011) CX3CR1Deficiency Leads to Impairment of Hippocampal Cognitive Function and Synaptic Plasticity. Journal of Neuroscience 31:16241-16250.

Sriram K, Matheson J M, Benkovic S A, Miller D B, Luster M I, O'Callaghan J P (2002) Mice deficient in TNF receptors are protected against dopaminergic neurotoxicity: implications for Parkinson's disease. The FASEB journal: official publication of the Federation of American Societies for Experimental Biology 16:1474-1476.

Tieu K, Ischiropoulos H, Przedborski S (2003) Nitric oxide and reactive oxygen species in Parkinson's disease. IUBMB Life 55:329-335.

Vroon A, Drukarch B, Bol J G J M, Cras P, Breve J J P, Allan S M, Raton J K, Hoogland P V J M, Van Dam A-M (2007) Neuroinflammation in Parkinson's patients and MPTP-treated mice is not restricted to the nigrostriatal system: microgliosis and differential expression of interleukin-1 receptors in the olfactory bulb. Experimental gerontology 42:762-771. West M J, Slomianka L, Gundersen H J (1991) Unbiased stereological estimation of the total number of neurons in the subdivisions of the rat hippocampus using the optical fractionator. Anat Rec 231:482-497.

Wu D C, Teistnann P, Tieu K, Vila M, Jackson-Lewis V, Ischiropoulos H, Przedborski S (2003) NADPH oxidase mediates oxidative stress in the 1-methyl-4-phenyl-1,2,3,6-tetrahydropyridine model of Parkinson's disease. Proceedings of the National Academy of Sciences of the United States of America 100:6145-6150.

Wu D C, Jackson-Lewis V, Vila M, Tieu K, Teismann P, Vadseth C, Choi D-K, Ischiropoulos H, Przedborski 5 (2002) Blockade of microglial activation is neuroprotective in the 1-methyl-4-phenyl-1,2,3,6-tetrahydropyridine mouse model of Parkinson disease. J Neurosci 22:1763-1771.

Wynne A M, Henry C J, Huang Y, Cleland A, Godbout J P (2010) Protracted downregulation of CX3CR1 on microglia of aged mice after lipopolysaccharide challenge. Brain, behavior, and immunity 24:1190-1201.

Yasuda Y, Shimoda T, Uno K, Tateishi N, Furuya S, Yagi K, Suzuki K, Fujita (2008) The effects of MPTP on the activation of microglia/astrocytes and cytokine/chemokine levels in different mice strains. Journal of Neuroimmunology 204:43-51.

Zolotukhin S. Potter M, Zolotukhin I, Sakai Y, Loiler S. Fraites T J, Chiodo V A, Phillipsberg T, Muzyczka N, Hauswirth W W, Flotte T R, Byrne B J, Snyder R O (2002) Production and purification of serotype 1, 2, and 5 recombinant adeno-associated viral vectors. Methods 28:158-167.

Zujovic V. Benavides J, Vigé X, Carter C, Taupin V (2000) Fractalkine modulates TNF-alpha secretion and neurotoxicity induced by microglial activation. Glia 29:305-315.

Zujovic V. Schussler N, Jourdain D, Duverger D, Taupin V (2001) In vivo neutralization of endogenous brain fractalkine increases hippocampal TNFalpha and 8-isoprostane production induced by intracerebroventricular injection of UPS. Journal of Neuroimmunology 115:135-143.

---

We claim:

1. A method of treating neurodegeneration, wherein the method comprises administering to nervous tissue cells in the brain of a mouse or human subject in need of such treatment an effective amount of a pharmaceutical composition comprising a rAAV9vector that comprises a nucleicacid molecule encoding a soluble fractalkine peptide as set forth in SEQ ID NO: 7 or SEQ ID NO: 10, respectively, wherein the nucleicacid molecule is operably linked to a nervous tissue cell-specific promoterand wherein the administration of the rAAV9 vector is selected from the group consisting of intravenous, intracranial, intracerebroventricular, intrathecal, and subarachnoidal injection such that the nucleicacid molecule is expressed in the nervous tissue cells in the brain and neurodegeneration is treated.

2. The method according to claim 1, wherein the pharmaceutical composition is administered to neuronal cells.

3. The method according to claim 1, wherein the subject has Parkinson's disease.

* * * * *

SEQUENCE LISTING

```
<160> NUMBER OF SEQ ID NOS: 11

<210> SEQ ID NO 1
<211> LENGTH: 35
<212> TYPE: DNA
<213> ORGANISM: Artificial Sequence
<220> FEATURE:
<223> OTHER INFORMATION: Sequence is synthesized

<400> SEQUENCE: 1
gagaccggtc caccatggct ccctcgccgc tcgcg                              35

<210> SEQ ID NO 2
<211> LENGTH: 78
<212> TYPE: DNA
<213> ORGANISM: Artificial Sequence
<220> FEATURE:
<223> OTHER INFORMATION: Sequence is synthesized

<400> SEQUENCE: 2
ctcgctagct cacatggcat agtcaggcac gtcataagga tagctagaag ccattgtggc    60
tgcctgggtg tcggggac                                                 78

<210> SEQ ID NO 3
<211> LENGTH: 38
<212> TYPE: DNA
<213> ORGANISM: Artificial Sequence
<220> FEATURE:
<223> OTHER INFORMATION: Sequence is synthesized

<400> SEQUENCE: 3
gtagccccac tgcctgggca gctgtggctg cctgggtg                           38
```

<210> SEQ ID NO 4
<211> LENGTH: 80
<212> TYPE: DNA
<213> ORGANISM: Artificial Sequence
<220> FEATURE:
<223> OTHER INFORMATION: Sequence is synthesized

<400> SEQUENCE: 4
ctcgctagct cacatggcat agtcaggcac gtcataagga tagctagaag ccatcactgg    60
caccaggacg tatgagttac                                                80

<210> SEQ ID NO 5
<211> LENGTH: 38
<212> TYPE: DNA
<213> ORGANISM: Artificial Sequence
<220> FEATURE:
<223> OTHER INFORMATION: Sequence is synthesized

<400> SEQUENCE: 5
cacccaggca gccacagctg cccaggcagt ggggctac                             38

<210> SEQ ID NO 6
<211> LENGTH: 395
<212> TYPE: PRT
<213> ORGANISM: Mus musculus

<400> SEQUENCE: 6

Met Ala Pro Ser Pro Leu Ala Trp Leu Leu Arg Leu Ala Ala Phe Phe
1               5                   10                  15

His Leu Cys Thr Leu Leu Pro Gly Gln His Leu Gly Met Thr Lys Cys
            20                  25                  30

Glu Ile Met Cys Asp Lys Met Thr Ser Arg Ile Pro Val Ala Leu Leu
        35                  40                  45

Ile Arg Tyr Gln Leu Asn Gln Glu Ser Cys Gly Lys Arg Ala Ile Val
    50                  55                  60

Leu Glu Thr Thr Gln His Arg Arg Phe Cys Ala Asp Pro Lys Glu Lys
65                  70                  75                  80

Trp Val Gln Asp Ala Met Lys His Leu Asp His Gln Ala Ala Ala Leu
                85                  90                  95

Thr Lys Asn Gly Gly Lys Phe Glu Lys Arg Val Asp Asn Val Thr Pro
            100                 105                 110

Gly Ile Thr Leu Ala Thr Arg Gly Leu Ser Pro Ser Ala Leu Thr Lys
        115                 120                 125

Pro Glu Ser Ala Thr Leu Glu Asp Leu Ala Leu Glu Leu Thr Thr Ile
    130                 135                 140

Ser Gln Glu Ala Arg Gly Thr Met Gly Thr Ser Gln Glu Pro Pro Ala
145                 150                 155                 160

Ala Val Thr Gly Ser Ser Leu Ser Thr Ser Glu Ala Gln Asp Ala Gly
                165                 170                 175

Leu Thr Ala Lys Pro Gln Ser Ile Gly Ser Phe Glu Ala Ala Asp Ile
            180                 185                 190

Ser Thr Thr Val Trp Pro Ser Pro Ala Val Tyr Gln Ser Gly Ser Ser
        195                 200                 205

Ser Trp Ala Glu Glu Lys Ala Thr Glu Ser Pro Ser Thr Thr Ala Pro
    210                 215                 220

Ser Pro Gln Val Ser Thr Thr Ser Pro Ser Thr Pro Glu Glu Asn Val
225                 230                 235                 240

```
Gly Ser Glu Gly Gln Pro Pro Trp Val Gln Gly Gln Asp Leu Ser Pro
                245                 250                 255

Glu Lys Ser Leu Gly Ser Glu Glu Ile Asn Pro Val His Thr Asp Asn
            260                 265                 270

Phe Gln Glu Arg Gly Pro Gly Asn Thr Val His Pro Ser Val Ala Pro
        275                 280                 285

Ile Ser Ser Glu Glu Thr Pro Ser Pro Glu Leu Val Ala Ser Gly Ser
    290                 295                 300

Gln Ala Pro Lys Ile Glu Pro Ile His Ala Thr Ala Asp Pro Gln
305                 310                 315                 320

Lys Leu Ser Val Leu Ile Thr Pro Val Pro Asp Thr Gln Ala Ala Thr
                325                 330                 335

Arg Arg Gln Ala Val Gly Leu Leu Ala Phe Leu Gly Leu Leu Phe Cys
            340                 345                 350

Leu Gly Val Ala Met Phe Ala Tyr Gln Ser Leu Gln Gly Cys Pro Arg
        355                 360                 365

Lys Met Ala Gly Glu Met Val Glu Gly Leu Arg Tyr Val Pro Arg Ser
    370                 375                 380

Cys Gly Ser Asn Ser Tyr Val Leu Val Pro Val
385                 390                 395

<210> SEQ ID NO 7
<211> LENGTH: 336
<212> TYPE: PRT
<213> ORGANISM: Mus musculus

<400> SEQUENCE: 7

Met Ala Pro Ser Pro Leu Ala Trp Leu Leu Arg Leu Ala Ala Phe Phe
1               5                   10                  15

His Leu Cys Thr Leu Leu Pro Gly Gln His Leu Gly Met Thr Lys Cys
            20                  25                  30

Glu Ile Met Cys Asp Lys Met Thr Ser Arg Ile Pro Val Ala Leu Leu
        35                  40                  45

Ile Arg Tyr Gln Leu Asn Gln Glu Ser Cys Gly Lys Arg Ala Ile Val
    50                  55                  60

Leu Glu Thr Thr Gln His Arg Arg Phe Cys Ala Asp Pro Lys Glu Lys
65                  70                  75                  80

Trp Val Gln Asp Ala Met Lys His Leu Asp His Gln Ala Ala Ala Leu
                85                  90                  95

Thr Lys Asn Gly Gly Lys Phe Glu Lys Arg Val Asp Asn Val Thr Pro
            100                 105                 110

Gly Ile Thr Leu Ala Thr Arg Gly Leu Ser Pro Ser Ala Leu Thr Lys
        115                 120                 125

Pro Glu Ser Ala Thr Leu Glu Asp Leu Ala Leu Glu Leu Thr Thr Ile
    130                 135                 140

Ser Gln Glu Ala Arg Gly Thr Met Gly Thr Ser Gln Glu Pro Pro Ala
145                 150                 155                 160

Ala Val Thr Gly Ser Ser Leu Ser Thr Ser Glu Ala Gln Asp Ala Gly
                165                 170                 175

Leu Thr Ala Lys Pro Gln Ser Ile Gly Ser Phe Glu Ala Ala Asp Ile
            180                 185                 190

Ser Thr Thr Val Trp Pro Ser Pro Ala Val Tyr Gln Ser Gly Ser Ser
        195                 200                 205

Ser Trp Ala Glu Glu Lys Ala Thr Glu Ser Pro Ser Thr Thr Ala Pro
    210                 215                 220
```

```
Ser Pro Gln Val Ser Thr Thr Ser Pro Ser Thr Pro Glu Glu Asn Val
225                 230                 235                 240

Gly Ser Glu Gly Gln Pro Pro Trp Val Gln Gly Gln Asp Leu Ser Pro
            245                 250                 255

Glu Lys Ser Leu Gly Ser Glu Glu Ile Asn Pro Val His Thr Asp Asn
        260                 265                 270

Phe Gln Glu Arg Gly Pro Gly Asn Thr Val His Pro Ser Val Ala Pro
            275                 280                 285

Ile Ser Ser Glu Glu Thr Pro Ser Pro Glu Leu Val Ala Ser Gly Ser
        290                 295                 300

Gln Ala Pro Lys Ile Glu Pro Ile His Ala Thr Ala Asp Pro Gln
305                 310                 315                 320

Lys Leu Ser Val Leu Ile Thr Pro Val Pro Asp Thr Gln Ala Ala Thr
                325                 330                 335

<210> SEQ ID NO 8
<211> LENGTH: 395
<212> TYPE: PRT
<213> ORGANISM: Mus musculus

<400> SEQUENCE: 8

Met Ala Pro Ser Pro Leu Ala Trp Leu Leu Arg Leu Ala Ala Phe Phe
1               5                   10                  15

His Leu Cys Thr Leu Leu Pro Gly Gln His Leu Gly Met Thr Lys Cys
                20                  25                  30

Glu Ile Met Cys Asp Lys Met Thr Ser Arg Ile Pro Val Ala Leu Leu
            35                  40                  45

Ile Arg Tyr Gln Leu Asn Gln Glu Ser Cys Gly Lys Arg Ala Ile Val
        50                  55                  60

Leu Glu Thr Thr Gln His Arg Arg Phe Cys Ala Asp Pro Lys Glu Lys
65                  70                  75                  80

Trp Val Gln Asp Ala Met Lys His Leu Asp His Gln Ala Ala Ala Leu
                85                  90                  95

Thr Lys Asn Gly Gly Lys Phe Glu Lys Arg Val Asp Asn Val Thr Pro
            100                 105                 110

Gly Ile Thr Leu Ala Thr Arg Gly Leu Ser Pro Ser Ala Leu Thr Lys
        115                 120                 125

Pro Glu Ser Ala Thr Leu Glu Asp Leu Ala Leu Glu Leu Thr Thr Ile
130                 135                 140

Ser Gln Glu Ala Arg Gly Thr Met Gly Thr Ser Gln Glu Pro Pro Ala
145                 150                 155                 160

Ala Val Thr Gly Ser Ser Leu Ser Thr Ser Glu Ala Gln Asp Ala Gly
                165                 170                 175

Leu Thr Ala Lys Pro Gln Ser Ile Gly Ser Phe Glu Ala Ala Asp Ile
            180                 185                 190

Ser Thr Thr Val Trp Pro Ser Pro Ala Val Tyr Gln Ser Gly Ser Ser
        195                 200                 205

Ser Trp Ala Glu Glu Lys Ala Thr Glu Ser Pro Ser Thr Thr Ala Pro
210                 215                 220

Ser Pro Gln Val Ser Thr Thr Ser Pro Ser Thr Pro Glu Glu Asn Val
225                 230                 235                 240

Gly Ser Glu Gly Gln Pro Pro Trp Val Gln Gly Gln Asp Leu Ser Pro
            245                 250                 255

Glu Lys Ser Leu Gly Ser Glu Glu Ile Asn Pro Val His Thr Asp Asn
```

```
            260                 265                 270
Phe Gln Glu Arg Gly Pro Gly Asn Thr Val His Pro Ser Val Ala Pro
            275                 280                 285

Ile Ser Ser Glu Glu Thr Pro Ser Pro Glu Leu Val Ala Ser Gly Ser
            290                 295                 300

Gln Ala Pro Lys Ile Glu Pro Ile His Ala Thr Ala Asp Pro Gln
305                 310                 315                 320

Lys Leu Ser Val Leu Ile Thr Pro Val Pro Asp Thr Gln Ala Ala Thr
                        325                 330                 335

Ala Ala Gln Ala Val Gly Leu Leu Ala Phe Leu Gly Leu Leu Phe Cys
            340                 345                 350

Leu Gly Val Ala Met Phe Ala Tyr Gln Ser Leu Gln Gly Cys Pro Arg
            355                 360                 365

Lys Met Ala Gly Glu Met Val Glu Gly Leu Arg Tyr Val Pro Arg Ser
            370                 375                 380

Cys Gly Ser Asn Ser Tyr Val Leu Val Pro Val
385                 390                 395

<210> SEQ ID NO 9
<211> LENGTH: 397
<212> TYPE: PRT
<213> ORGANISM: Homo sapiens

<400> SEQUENCE: 9

Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
                20                  25                  30

Asn Ile Thr Cys Ser Lys Met Thr Ser Lys Ile Pro Val Ala Leu Leu
            35                  40                  45

Ile His Tyr Gln Gln Asn Gln Ala Ser Cys Gly Lys Arg Ala Ile Ile
        50                  55                  60

Leu Glu Thr Arg Gln His Arg Leu Phe Cys Ala Asp Pro Lys Glu Gln
65                  70                  75                  80

Trp Val Lys Asp Ala Met Gln His Leu Asp Arg Gln Ala Ala Ala Leu
                85                  90                  95

Thr Arg Asn Gly Gly Thr Phe Glu Lys Gln Ile Gly Glu Val Lys Pro
            100                 105                 110

Arg Thr Thr Pro Ala Ala Gly Gly Met Asp Glu Ser Val Val Leu Glu
        115                 120                 125

Pro Glu Ala Thr Gly Glu Ser Ser Leu Glu Pro Thr Pro Ser Ser
130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Pro Val Ser
            180                 185                 190

Thr Ala Ala Thr Trp Gln Ser Ser Ala Pro His Gln Pro Gly Pro Ser
        195                 200                 205

Leu Trp Ala Glu Ala Lys Thr Ser Glu Ala Pro Ser Thr Gln Asp Pro
210                 215                 220

Ser Thr Gln Ala Ser Thr Ala Ser Ser Pro Ala Pro Glu Glu Asn Ala
225                 230                 235                 240
```

-continued

```
Pro Ser Glu Gly Gln Arg Val Trp Gly Gln Gly Gln Ser Pro Arg Pro
            245                 250                 255

Glu Asn Ser Leu Glu Arg Glu Glu Met Gly Pro Val Pro Ala His Thr
        260                 265                 270

Asp Ala Phe Gln Asp Trp Gly Pro Gly Ser Met Ala His Val Ser Val
    275                 280                 285

Val Pro Val Ser Ser Glu Gly Thr Pro Ser Arg Glu Pro Val Ala Ser
290                 295                 300

Gly Ser Trp Thr Pro Lys Ala Glu Glu Pro Ile His Ala Thr Met Asp
305                 310                 315                 320

Pro Gln Arg Leu Gly Val Leu Ile Thr Pro Val Pro Asp Ala Gln Ala
                325                 330                 335

Ala Thr Arg Arg Gln Ala Val Gly Leu Leu Ala Phe Leu Gly Leu Leu
            340                 345                 350

Phe Cys Leu Gly Val Ala Met Phe Thr Tyr Gln Ser Leu Gln Gly Cys
        355                 360                 365

Pro Arg Lys Met Ala Gly Glu Met Ala Glu Gly Leu Arg Tyr Ile Pro
    370                 375                 380

Arg Ser Cys Gly Ser Asn Ser Tyr Val Leu Val Pro Val
385                 390                 395

<210> SEQ ID NO 10
<211> LENGTH: 341
<212> TYPE: PRT
<213> ORGANISM: Homo sapiens

<400> SEQUENCE: 10

Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
            20                  25                  30

Asn Ile Thr Cys Ser Lys Met Thr Ser Lys Ile Pro Val Ala Leu Leu
        35                  40                  45

Ile His Tyr Gln Gln Asn Gln Ala Ser Cys Gly Lys Arg Ala Ile Ile
    50                  55                  60

Leu Glu Thr Arg Gln His Arg Leu Phe Cys Ala Asp Pro Lys Glu Gln
65                  70                  75                  80

Trp Val Lys Asp Ala Met Gln His Leu Asp Arg Gln Ala Ala Ala Leu
                85                  90                  95

Thr Arg Asn Gly Gly Thr Phe Glu Lys Gln Ile Gly Glu Val Lys Pro
            100                 105                 110

Arg Thr Thr Pro Ala Ala Gly Gly Met Asp Glu Ser Val Val Leu Glu
        115                 120                 125

Pro Glu Ala Thr Gly Glu Ser Ser Leu Glu Pro Thr Pro Ser Ser
    130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Pro Val Ser
            180                 185                 190

Thr Ala Ala Thr Trp Gln Ser Ser Ala Pro His Gln Pro Gly Pro Ser
        195                 200                 205

Leu Trp Ala Glu Ala Lys Thr Ser Glu Ala Pro Ser Thr Gln Asp Pro
    210                 215                 220
```

```
Ser Thr Gln Ala Ser Thr Ala Ser Ser Pro Ala Pro Glu Glu Asn Ala
225                 230                 235                 240

Pro Ser Glu Gly Gln Arg Val Trp Gly Gln Gly Gln Ser Pro Arg Pro
                245                 250                 255

Glu Asn Ser Leu Glu Arg Glu Met Gly Pro Val Pro Ala His Thr
            260                 265                 270

Asp Ala Phe Gln Asp Trp Gly Pro Gly Ser Met Ala His Val Ser Val
            275                 280                 285

Val Pro Val Ser Ser Glu Gly Thr Pro Ser Arg Glu Pro Val Ala Ser
            290                 295                 300

Gly Ser Trp Thr Pro Lys Ala Glu Glu Pro Ile His Ala Thr Met Asp
305                 310                 315                 320

Pro Gln Arg Leu Gly Val Leu Ile Thr Pro Val Pro Asp Ala Gln Ala
                325                 330                 335

Ala Thr Arg Arg Gln
            340

<210> SEQ ID NO 11
<211> LENGTH: 397
<212> TYPE: PRT
<213> ORGANISM: Homo sapiens

<400> SEQUENCE: 11

Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
                20                  25                  30

Asn Ile Thr Cys Ser Lys Met Thr Ser Lys Ile Pro Val Ala Leu Leu
            35                  40                  45

Ile His Tyr Gln Gln Asn Gln Ala Ser Cys Gly Lys Arg Ala Ile Ile
        50                  55                  60

Leu Glu Thr Arg Gln His Arg Leu Phe Cys Ala Asp Pro Lys Glu Gln
65                  70                  75                  80

Trp Val Lys Asp Ala Met Gln His Leu Asp Arg Gln Ala Ala Ala Leu
                85                  90                  95

Thr Arg Asn Gly Gly Thr Phe Glu Lys Gln Ile Gly Glu Val Lys Pro
            100                 105                 110

Arg Thr Thr Pro Ala Ala Gly Gly Met Asp Glu Ser Val Val Leu Glu
        115                 120                 125

Pro Glu Ala Thr Gly Glu Ser Ser Ser Leu Glu Pro Thr Pro Ser Ser
130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Val Ser
            180                 185                 190

Thr Ala Ala Thr Trp Gln Ser Ser Ala Pro His Gln Pro Gly Pro Ser
        195                 200                 205

Leu Trp Ala Glu Ala Lys Thr Ser Glu Ala Pro Ser Thr Gln Asp Pro
210                 215                 220

Ser Thr Gln Ala Ser Thr Ala Ser Ser Pro Ala Pro Glu Glu Asn Ala
225                 230                 235                 240

Pro Ser Glu Gly Gln Arg Val Trp Gly Gln Gly Gln Ser Pro Arg Pro
```

-continued

```
                245                 250                 255
Glu Asn Ser Leu Glu Arg Glu Glu Met Gly Pro Val Pro Ala His Thr
            260                 265                 270

Asp Ala Phe Gln Asp Trp Gly Pro Gly Ser Met Ala His Val Ser Val
            275                 280                 285

Val Pro Val Ser Ser Glu Gly Thr Pro Ser Arg Glu Pro Val Ala Ser
    290                 295                 300

Gly Ser Trp Thr Pro Lys Ala Glu Glu Pro Ile His Ala Thr Met Asp
305                 310                 315                 320

Pro Gln Arg Leu Gly Val Leu Ile Thr Pro Val Pro Asp Ala Gln Ala
                325                 330                 335

Ala Thr Ala Ala Gln Ala Val Gly Leu Leu Ala Phe Leu Gly Leu Leu
            340                 345                 350

Phe Cys Leu Gly Val Ala Met Phe Thr Tyr Gln Ser Leu Gln Gly Cys
            355                 360                 365

Pro Arg Lys Met Ala Gly Glu Met Ala Glu Gly Leu Arg Tyr Ile Pro
    370                 375                 380

Arg Ser Cys Gly Ser Asn Ser Tyr Val Leu Val Pro Val
385                 390                 395
```